United States Patent

Suzuki et al.

Patent Number: 5,468,756
Date of Patent: Nov. 21, 1995

[54] IMIDAZONAPHTHYRIDINE DERIVATIVES

[75] Inventors: Fumio Suzuki, Mishima; Takeshi Kuroda, Shizuoka; Shigeto Kitamura, Machida; Kenji Ohmori, Mishima, all of Japan

[73] Assignee: Kyowa Hakko Kogyo Co., Ltd., Tokyo, Japan

[21] Appl. No.: 241,631

[22] Filed: May 12, 1994

Related U.S. Application Data

[62] Division of Ser. No. 999,658, Dec. 29, 1992, Pat. No. 5,364,859, which is a continuation of Ser. No. 706,852, May 29, 1991, abandoned.

[30] Foreign Application Priority Data

Jun. 1, 1990 [JP] Japan ............ 2-143460
Nov. 30, 1990 [JP] Japan ............ 2-334657

[51] Int. Cl.$^6$ .................. C07D 471/00; A61K 31/44
[52] U.S. Cl. ............................... 514/293; 546/82
[58] Field of Search ...................... 546/82; 514/293

[56] References Cited

U.S. PATENT DOCUMENTS

| | | | |
|---|---|---|---|
| Re. 30,456 | 12/1980 | Omodei-Sale | 546/82 |
| 4,059,584 | 11/1977 | Kadin | 546/82 |
| 4,689,338 | 8/1987 | Gerster | 514/293 |
| 4,698,348 | 10/1987 | Gerster | 514/293 |
| 4,760,073 | 7/1988 | Blythin et al. | 546/82 |

FOREIGN PATENT DOCUMENTS

| 0145340 | 6/1985 | European Pat. Off. . |
|---|---|---|
| 0302303 | 2/1989 | European Pat. Off. . |

*Primary Examiner*—Gary L. Geist
*Assistant Examiner*—Catherine Scalzo
*Attorney, Agent, or Firm*—Fitzpatrick, Cella, Harper & Scinto

[57] ABSTRACT

Disclosed are imidazonaphthyridine derivatives represented by formula (I)

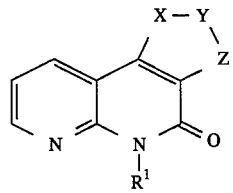

(I)

wherein:
  $R^1$ represents lower alkyl or substituted or unsubstituted aryl; and
  X—Y—Z represents

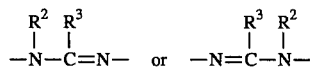

wherein $R^2$ represents hydrogen, lower alkyl, alkenyl, aralkenyl, or —C ($R^5$)H—(CH$_2$)$_n$—$R^4$ (wherein $R^4$ represents substituted or unsubstituted aryl, substituted or unsubstituted pyridyl, substituted or unsubstituted furyl, hydroxy-substituted lower alkyl, lower alkanoyloxy, morpholino, lower alkanoyl, carboxy, lower alkoxycarbonyl, cycloalkyl, hydroxy, lower alkoxy, halogen or NR$^6$R$^7$ wherein R$^6$ and R$^7$ independently represents hydrogen or lower alkyl; R$^5$ represents hydrogen, lower alkyl, or phenyl; and n represents an integer of 0 to 3); and $R^3$ represents hydrogen, mercapto, hydroxy, lower alkyl, or aryl
and pharmaceutically acceptable salts thereof.

The compounds show a potent anti-inflammatory, anti-allergic and broncho-dilative activity.

7 Claims, No Drawings

IMIDAZONAPHTHYRIDINE DERIVATIVES

BACKGROUND OF THE INVENTION

This application is a division of application Ser. No. 07/999,658, now U.S. Pat. No. 5,364,859 issued Nov. 15, 1994 filed Dec. 29, 1992, which is a continuation of application Ser. No. 07/706,852, filed May 29, 1991, now abandoned.

The present invention relates to novel imidazonaphthyridine derivatives having 1H,5H- or 3H,5H-imidazo-[4,5-c][1,8]naphthyridin-4-one skeleton and which show an anti-inflammatory activity, an anti-allergic activity and a broncho-dilative activity.

Imidazo[4,5-c]quinoline derivatives having a broncho-dilative and antiviral activity are disclosed in Japanese Published Unexamined Patent Application No. 123488/85 (U.S. Pat. Nos. 4,698,348 and 4,689,338 and EP-A-145340). However, 1H,5H- or 3H,5H-imidazo[4,5-c][1,8]naphthyridin- 4-one derivatives and their pharmacological activity are unknown.

SUMMARY OF THE INVENTION

An object of the present invention is to provide novel imidazonaphthyridine derivatives having a potent anti-inflammatory, anti-allergic and broncho-dilative activity.

The present invention relates to imidazonaphthyridine derivatives represented by formula (I):

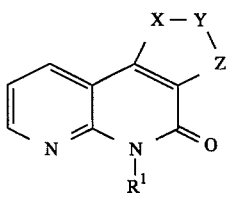

wherein $R^1$ represents lower alkyl or substituted or unsubstituted aryl; and X—Y—Z represents

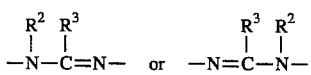

wherein $R^2$ represents hydrogen, lower alkyl, alkenyl, aralkenyl, or —C($R^5$)H—(CH$_2$)$_n$—$R^4$ (wherein $R^4$ represents substituted or unsubstituted aryl, substituted or unsubstituted pyridyl, substituted or unsubstituted furyl, hydroxy-substituted lower alkyl, lower alkanoyloxy, morpholino. lower alkanoyl, carboxy, lower alkoxycarbonyl, cycloalkyl, hydroxy, lower alkoxy, halogen or $NR^6R^7$ wherein $R^6$ and $R^7$ independently represents hydrogen or lower alkyl; $R^5$ represents hydrogen, lower alkyl, or phenyl; and n represents an integer of 0 to 3); and $R^3$ represents hydrogen, mercapto, hydroxy, lower alkyl, or aryl and pharmaceutically acceptable salts thereof.

The compounds represented by formula (I) are hereinafter referred to as Compounds (I); the same applies to the compounds of other formula numbers.

DETAILED DESCRIPTION OF THE INVENTION

In the definitions of the groups in formula (I), the lower alkyl and the alkyl moiety in the hydroxy-substituted lower alkyl and the lower alkoxy mean a straight-chain or branched alkyl group having 1 to 8 carbon atoms, for example, methyl, ethyl, propyl, isopropyl, butyl, isobutyl, sec-butyl, tert-butyl, pentyl, neopentyl, hexyl, heptyl and octyl. The aryl means an aryl group having 6 to 10 carbon atoms such as phenyl and naphthyl. The alkenyl means an alkenyl group having 2 to 6 carbon atoms such as vinyl, allyl, propenyl, butenyl and hexenyl. The aralkenyl means an aralkenyl group having 8 to 18 carbon atoms such as styryl and cinnamyl. The lower alkanoyl and the alkanoyl moiety in the lower alkanoyloxy mean a straight-chain or branched alkanoyl group having 1 to 6 carbon atoms such as formyl, acetyl, propionyl, butyryl, isobutyryl, valeryl, isovaleryl, pivaloyl and hexanoyl. The cycloalkyl means a cycloalkyl group having 3 to 8 carbon atoms such as cyclopropyl, cyclopentyl, cyclohexyl and cyclooctyl.

The aryl, pyridyl and furyl may be substituted by one to three substituents which are the same or different. Examples of the substituents are lower alkyl, lower alkoxy, nitro, lower alkoxycarbonyl and halogen. The definitions of the lower alkyl and the alkyl moiety in the lower alkoxy and the lower alkoxycarbonyl are the same as those of the lower alkyl and the alkyl moiety in the hydroxy-substituted lower alkyl and the lower alkoxy described above. Examples of the halogen include fluorine, chlorine, bromine and iodine.

Compounds (I) wherein $R^2$ is hydrogen are present as Compounds (I-1) and/or (I-2) which are tautomers, but in the following description, they are collectively referred to as Compounds (I-1).

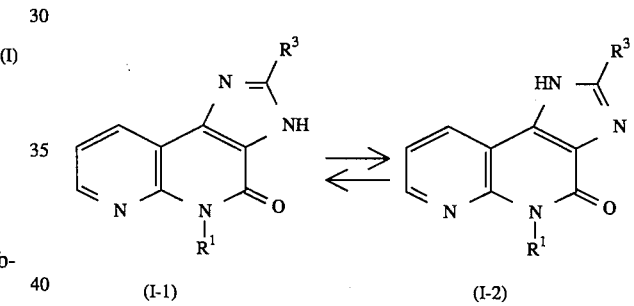

The pharmaceutically acceptable salts of Compounds (I) include acid addition salts, metal salts, ammonium salts, organic amine addition salts, and amino acid addition salts. As the pharmaceutically acceptable acid addition salts of Compounds (I), inorganic acid addition salts such as hydrochloride, sulfate and phosphate, and organic acid addition salts such as acetate, maleate, fumarate, tartrate and citrate may be mentioned. As the pharmaceutically acceptable metal salts, alkali metal salts such as sodium salt and potassium salt, alkaline earth metal salts such as magnesium salt and calcium salt, aluminum salt, and zinc salt may be mentioned. As the pharmaceutically acceptable organic amine addition salts, salts with morpholine and piperidine may be mentioned, and as the pharmaceutically acceptable amino acid addition salts, salts with lysine, glycine and phenylalanine may be mentioned.

The processes for preparing Compounds (I) are described below.

In the following processes, in cases where the defined groups change under the conditions shown or are inappropriate for practicing the processes, the processes can be readily carried out by applying thereto means conventionally used in organic synthetic chemistry, for example, protection of functional groups and elimination of protecting groups. Process 1

Compound (Ia) [Compound (I) wherein X—Y—Z is $$\begin{matrix} & R^2 & R^3 \\ & | & | \\ -N & -C = N - ] \end{matrix}$$

can be obtained by the following reaction steps.

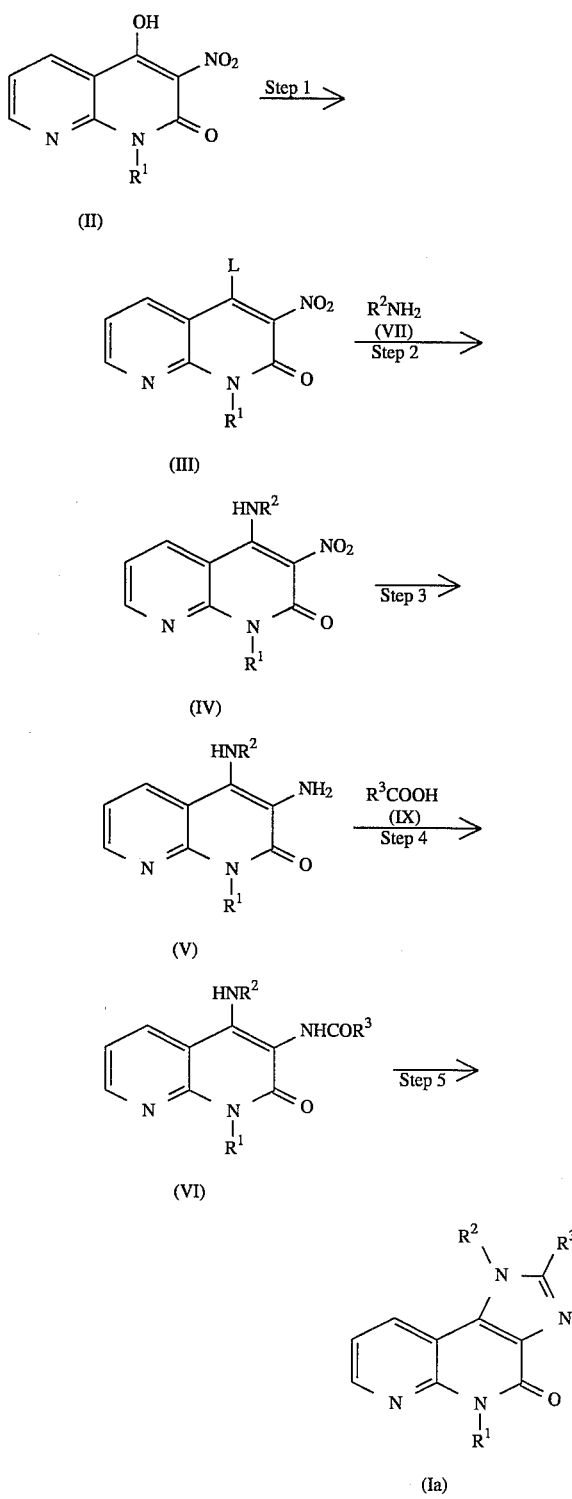

In the above formulae, L represents a leaving group, and $R^1$, $R^2$ and $R^3$ have the same significances as defined above.

Examples of the leaving group represented by L include a halogen atom such as chlorine, bromine or iodine, alkylsulfonyloxy such as methanesulfonyloxy, and arylsulfonyloxy such as phenylsulfonyloxy or p-toluenesulfonyloxy.

The starting compound (II) can be synthesized by a known method [J. Heterocyclic Chem., 22, 193 (1985)] or by the method shown in Reference Example 1.

(Step 1)

Compound (IIIa) [Compound (III) wherein L is sulfonyloxy] can be obtained by allowing Compound (II) to react with sulfonyl chloride in the presence or absence of a base and a solvent.

Examples of the base are alkali metal carbonates such as potassium carbonate and sodium carbonate, alkali metal hydrides such as sodium hydride, alkali metal alkoxides such as sodium methoxide and sodium ethoxide, and alkylamines such as triethylamine.

As the reaction solvent, those which are inert to the reaction, for example, ethers such as tetrahydrofuran and dioxane, amides such as dimethylformamide, alcohols such as methanol and ethanol, hydrocarbons such as xylene, toluene, n-hexane and cyclohexane, haloalkanes such as chloroform and carbon tetrachloride, and dimethylsulfoxide, may be used alone or in combination.

As the sulfonyl chloride, alkylsulfonyl chloride such as methanesulfonyl chloride, arylsulfonyl chloride such as p-toluenesulfonyl chloride, etc. may be used.

The reaction is carried out at 0° to 100° C. and is completed in 5 minutes to 24 hours.

Compound (IIIb) [Compound (III) wherein L is halogen] can be obtained by allowing Compound (II) to react with a halogenating agent in the presence or absence of a solvent, if necessary, in the presence of a base.

The same base and solvent as mentioned above may be used.

As the halogenating agent, thionyl chloride, phosphorus oxychloride, phosphorus pentachloride, phosphorus tribromide, etc. may be used.

The reaction is carried out at 0° to 200° C. and is completed in 5 minutes to 24 hours.

(Step 2)

Compound (IV) can be obtained by allowing Compound (III) to react with amine (VII) [Compound (VII)] in the presence or absence of a solvent, if necessary, in the presence of a base.

Examples of the base are alkali metal carbonates such as potassium carbonate and sodium carbonate, alkali metal hydrides such as sodium hydride, alkali metal alkoxides such as sodium methoxide and sodium ethoxide, and alkylamines such as triethylamine.

As the reaction solvent, those which are inert to the reaction, for example, ethers such as tetrahydrofuran and dioxane, amides such as dimethylformamide, alcohols such as methanol and ethanol, hydrocarbons such as xylene, toluene, n-hexane and cyclohexane, haloalkanes such as chloroform and carbon tetrachloride, and dimethylsulfoxide may be used alone or in combination.

The reaction is carried out at 0° to 100° C. and is completed in 5 minutes to 24 hours.

(Step 3)

Compound (V) can be obtained by reducing Compound (IV) in a solvent.

Reduction is carried out, for example, by catalytic reduction using a catalyst such as palladium/carbon or platinum oxide; reduction using a metal such as iron or zinc; and reduction using a metal sulfur derivative such as sodium hydrosulfite.

As the reaction solvent, those which are inert to the reaction, for example, ethers such as tetrahydrofuran and dioxane, amides such as dimethylformamide, alcohols such as methanol and ethanol, acids such as hydrochloric acid, acetic acid and sulfuric acid, and water, may be used alone or in combination.

The reaction is carried out at 0° to 100° C. and is completed in 5 minutes to 24 hours.

(Step 4)

Compound (VI) can be obtained by allowing Compound (V) to react with carboxylic acid (IX) [Compound (IX)] or a reactive derivative thereof.

When Compound (IX) is used, it is preferred to carry out the reaction in the presence of a condensing agent. As the condensing agent, thionyl chloride, N,N'-dicyclohexylcarbodiimide (DCC), polyphosphoric acid, etc. may be used. Examples of the reactive derivative are acid halides such as acid chloride and acid bromide, acid anhydrides, mixed acid anhydrides formed with ethyl chlorocarbonate, isobutyl chlorocarbonate, etc., activated esters such as p-nitrophenyl ester and N-oxysuccinimide ester, and ortho esters.

The reaction is carried out at −10° to 50° C. and is completed in 5 minutes to 24 hours.

(Step 5)

Compound (Ia) can be obtained by subjecting Compound (VI) to reaction in the presence or absence of a solvent, if necessary, in the presence of a cyclizing agent.

Examples of the reaction solvent include hexamethylphosphoramide, diphenyl ether, glycerine triethyl ether, butyl ether, isoamyl ether, diethylene glycol, triethylene glycol, and Dowsam A (Dow Chemical Co., Ltd.). Examples of the cyclizing agent include polyphosphoric acid, polyphosphoric acid ester, sulfuric acid, acetic acid, phosphorus pentoxide, phosphorus oxychloride, phosphorus trichloride, phosphorus tribromide, phosphorus pentachloride, and thionyl chloride.

The reaction is carried out at 50° to 250° C., preferably 100° to 250° C. and is completed in 5 minutes to 24 hours.

Process 2

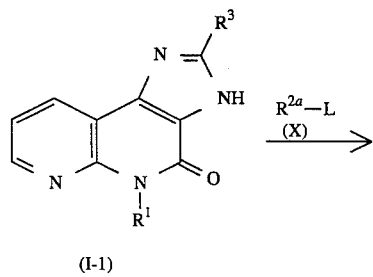

(I-1)

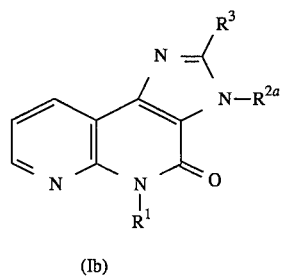

(Ib)

In the above formulae, $R^{2a}$ represents $R^2$ as defined above with the exception of hydrogen; and $R^1$, $R^3$ and L have the same significances as defined above.

Compound (Ib) [Compound (I) wherein X—Y—Z is

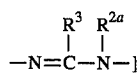

can be prepared by allowing Compound (I-1) to react with Compound (X) in the presence or absence of a solvent, preferably in the presence of a base.

The same solvent and base as in Step 1 of Process 1 may be used.

The reaction is carried out at 0° to 200° C. and is completed in 5 minutes to 24 hours.

Process 3

Compound (Iba) [Compound (Ib) wherein $R^3$ is hydroxy or mercapto] can also be obtained from Compound (V) obtained in Process 1 by the following method.

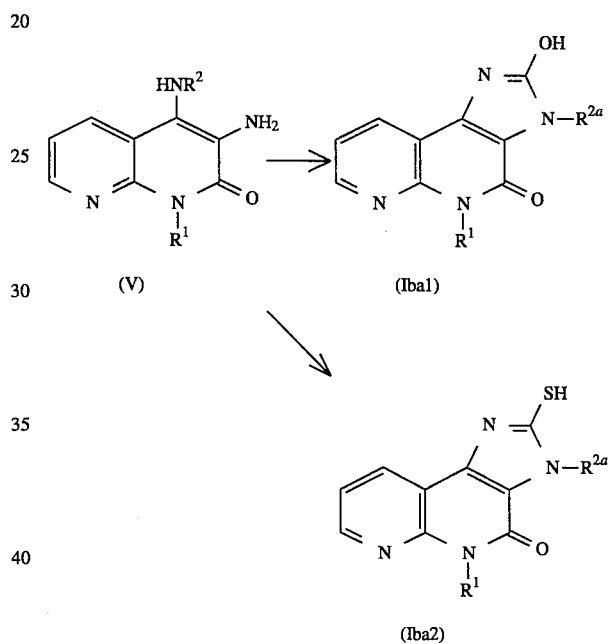

In the above formulae, $R^1$, $R^2$ and $R^{2a}$ have the same significances as defined above.

Compound (Iba1) [Compound (Iba) wherein $R^3$ is hydroxy] can be prepared by allowing Compound (V) to react with phosgene, carbonyldiimidazole, urea, or the like.

As the reaction solvent, those which are inert to the reaction, for example, alcohols such as methanol and ethanol, ethers such as tetrahydrofuran and dioxane, and halogenated hydrocarbons such as chloroform may be used alone or in combination.

The reaction is carried out at 0° to 150° C. and is completed in 30 minutes to 10 hours.

Compound (Iba2) [Compound (Iba) wherein $R^3$ is mercapto] can be obtained by allowing Compound (V) to react with thiophosgene, thiocarbonyldiimidazole, thiourea, or the like.

The reaction is carried out under the same conditions using the same solvent as in the process for preparing Compound (Iba1).

Process 4

Compound (Ic) is Compound (I) wherein X—Y—Z represents

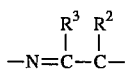

and $R^2$ is $-C(R^5)H-(CH_2)_n-R^4$.

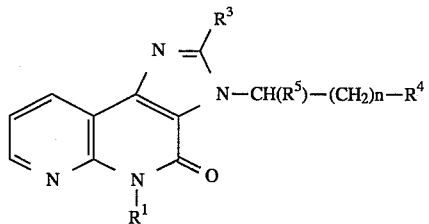

Compound (Ic2) [Compound (Ic) wherein $R^4$ is $NR^6R^7$ or morpholino] can be obtained by the following reaction step.

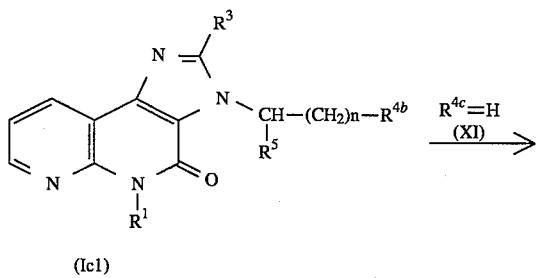

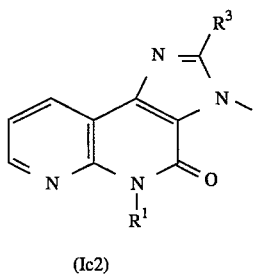

In the above formulae, $R^1$, $R^3$ and $R^5$ have the same significances as defined above; $R^{4b}$ represents halogen in the definition of $R^4$; and $R^{4c}$ represents $NR^6R^7$ or morpholino in the definition of $R^4$.

Compound (Ic2) can be obtained by allowing Compound (Ic1) to react with Compound (XI) in the presence or absence of a base and a solvent.

The same reaction solvent and base as in Step 1 of Process 1 may be used.

The reaction is carried out at 0° to 200° C. and is completed in 5 minutes to 24 hours.

Process 5

Compound (Ic3) [Compound (Ic) wherein $R^4$ is hydroxy] can be obtained by the following reaction step.

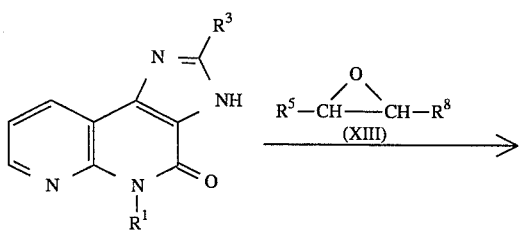

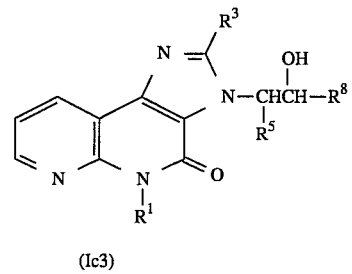

In the above formulae, $R^1$, $R^3$ and $R^5$ have the same significances as defined above; and $R^8$ is hydrogen or lower alkyl having 1 to 7 carbon atoms.

Compound (Ic3) can be obtained by allowing Compound (I-1) to react with Compound (XIII) in the presence or absence of a base and a solvent.

The same reaction solvent and base as in Process 1 may be used.

The reaction is carried out at 0° to 200° C. and is completed in 5 minutes to 24 hours.

The intermediates and the desired products in the processes described above can be isolated and purified by purification means conventionally used in organic synthetic chemistry, for example, filtration, extraction, washing, drying, concentration, recrystallization and various kinds of chromatography. The intermediates can be subjected to the subsequent reaction without particular purification.

In the case where a salt of Compound (I) is desired and it is produced in the form of the desired salt, it can be subjected to purification as such. In the case where Compound (I) is produced in the free state and its salt is desired, it can be converted into its salt in a conventional manner.

Compounds (I) and pharmaceutically acceptable salts thereof sometimes exist in the form of an addition product with water or with a solvent. Such addition products are also included within the scope of the present invention.

Specific examples of Compounds (I) obtained in the respective processes are shown in Table 1.

TABLE 1-1

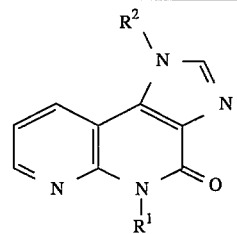

| Compound No. | $-R^2$ | $-R^1$ |
|---|---|---|
| 1 | $-CH_3$ | $-(CH_2)_3CH_3$ |
| 2 | " | —⟨phenyl⟩ |
| 5 | $-C_2H_5$ | " |
| 6 | $-CH(CH_3)_2$ | " |

TABLE 1-1-continued

[Structure: tricyclic with R² on imidazole N, R¹ on pyridone N, C=O]

| Compound No. | —R² | —R¹ |
|---|---|---|
| 7 | —CH₂—C₆H₅ | " |

TABLE 1-2

[Structure: pyrido-pyridone with substituent =N—C(R³)=N—R² at ring, R¹ on pyridone N]

| Compound No. | —R³ | —R² | —R¹ |
|---|---|---|---|
| 3 | —H | —H | —C₆H₅ |
| 4 | " | —CH₃ | " |
| 8 | " | —C₂H₅ | " |
| 9 | " | —(CH₂)₂CH₃ | " |
| 10 | " | —CH(CH₃)₂ | " |
| 11 | " | —(CH₂)₃CH₃ | " |
| 12 | " | —CH₂CH(CH₃)₂ | " |
| 13 | " | —CH₂—C₆H₅ | " |
| 14 | " | —CH₂COCH₃ | " |
| 15 | " | —CH₂CH₂—(pyridyl) | " |
| 16 | " | —CH(CH₃)—C₆H₅ | " |
| 17 | " | —CH₂COOH | " |
| 18 | —CH₃ | —H | " |
| 19 | —C₆H₅ | " | " |
| 20 | —SH | " | " |

TABLE 1-2-continued

[Structure: fused bicyclic pyridone core with substituents R¹ on N, R² and =N-R³ group at adjacent positions]

| Compound No. | —R³ | —R² | —R¹ |
|---|---|---|---|
| 21 | —OH | —H | phenyl |
| 22 | —H | " | 4-methoxyphenyl |
| 23 | " | " | 3-methoxyphenyl |
| 24 | " | " | 4-methylphenyl |
| 25 | " | " | 3-methylphenyl |
| 26 | " | " | 3-chlorophenyl |
| 27 | " | " | —(CH$_2$)$_3$CH$_3$ |
| 28 | " | —CH$_3$ | " |
| 29 | " | —(CH$_2$)$_2$CH$_3$ | " |
| 30 | " | —(CH$_2$)$_5$CH$_3$ | phenyl |
| 31 | " | —CH$_2$CH$_2$OCH$_2$CH$_3$ | " |
| 32 | " | —CH$_2$COOCH$_2$CH$_3$ | " |
| 33 | " | —CH$_2$CH=CH$_2$ | " |
| 34 | " | —CH$_2$CH$_2$OCOCH$_3$ | " |
| 35 | " | —CH(CH$_2$CH$_2$CH$_3$)$_2$ | " |
| 36 | " | —CH$_2$CH=CH—phenyl | " |
| 37 | " | —CH$_2$—cyclohexyl | " |

TABLE 1-2-continued

[Structure: pyrido-pyrimidinone core with R¹ on ring N, R² on exocyclic N, R³ on imine carbon]

| Compound No. | —R³ | —R² | —R¹ |
|---|---|---|---|
| 38 | " | —CH(C₆H₅)₂ (diphenylmethyl) | " |
| 39 | —H | —CH₂-(2,5-dimethylphenyl) | —C₆H₅ (phenyl) |
| 40 | " | —CH₂-(4-chlorophenyl) | " |
| 41 | " | —CH₂-(3-methylphenyl) | " |
| 42 | " | —CH₂-(4-nitrophenyl) | " |
| 43 | " | —CH₂-(4-methylphenyl) | " |
| 44 | " | —CH₂-(4-fluorophenyl) | " |
| 45 | " | —CH₂-(4-methoxyphenyl) | " |
| 46 | " | —CH₂-(3-methoxyphenyl) | " |

TABLE 1-2-continued
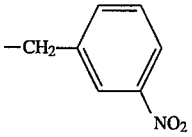
| Compound No. | −R³ | −R² | −R¹ |
|---|---|---|---|
| 47 | " | −CH₂−(3-nitrophenyl) | " |
| 48 | " | −CH₂−(2-chlorophenyl) | " |
| 49 | " | −CH₂−(3-bromophenyl) | " |
| 50 | " | −CH₂−(4-COOCH₃-phenyl) | " |
| 51 | " | −(CH₂)₂CH₂OH | " |
| 52 | −H | −CH₂CH(OH)CH₃ | phenyl |
| 53 | " | −CH₂−(2-furyl) | " |
| 54 | " | −CH₂−(3-pyridyl) | " |
| 55 | " | −CH₂−phenyl | 4-OCH₃-phenyl |
| 56 | " | " | 3-OCH₃-phenyl |
| 57 | " | " | 4-CH₃-phenyl |

TABLE 1-2-continued

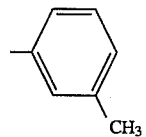

| Compound No. | —R³ | —R² | —R¹ |
|---|---|---|---|
| 58 | " | " | 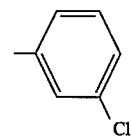 |
| 59 | " | " | 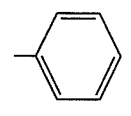 |
| 60 | —CH₃ | " | 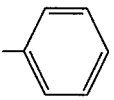 |
| 61 | 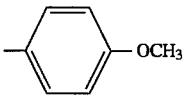 | " | " |
| 62 | —H | —CH₂CH(CH₃)₂ | 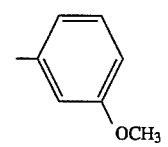 |
| 63 | " | " | 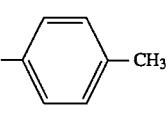 |
| 64 | " | " | 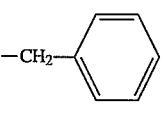 |
| 65 | —H | —CH₂CH(CH₃)₂ | 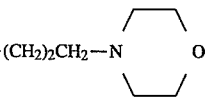 |
| 66 | " | —(CH₂)₂CH₂—N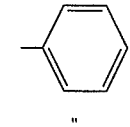O | " |
| 67 | " | —(CH₂)₂CH₂N(CH₂CH₃)₂ | " |
| 68 | " | —CH₂CH₂CH₂Cl | " |
| 69 | " | —CH₂CH₂CH₂I | " |

The pharmacological activities of Compounds (I) are illustrated below.

a) Effect on carrageenin-induced paw edema

Male Wistar rats weighing 150 to 160 g (n=3–5) were used in the experiment. After the right hind paw volume was measured with the plethysmograph (TK-101; Unicom Co., Ltd.), the test compound (25, 50 or 100 mg/kg) was orally administered. After one hour, 0.1 ml of 1% carrageenin (λ-carrageenin; PICNIN-A®, Zushi Kagaku Co., Ltd.) was subcutaneously injected into the right hind paw footpad. Three hours after the injection of carrageenin, the right hind paw volume was measured and the swelling rate was determined by the following equation 1.

$$\text{Swelling rate (\%)} = \frac{Vt - Vo}{Vo} \times 100 \quad (1)$$

Vt: the right hind paw volume measured 3 hours after the injection of carrageenin Vo: the right hind paw volume measured prior to the injection of carrageenin The suppression rate was calculated by the following equation 2.

$$\text{Suppression rate (\%)} = \frac{Swc - Swt}{Swc} \times 100 \quad (2)$$

Swt: the swelling rate of the group administered with the test compound

Swc: the swelling rate of the control group administered with physiological saline solution The results are shown in Table 2.

b) Effect on zymosan-induced paw edema

The experiment was carried out in the same manner as in the carrageenin-induced paw edema test except that 1% zymosan (Zymosan A®; Sigma Chemical Co.) was used in place of 1% carrageenin and the right hind paw volume was measured hours after the injection of the edema-inducing substance instead of 3 hours. The swelling rate and the suppression rate were calculated by equation 1 and equation 2, respectively. The results are shown in Table 2.

TABLE 2

| | Suppression rate for paw swelling (%) | |
|---|---|---|
| Compound | (a) Carrageenin-induced edema | (b) Zymosan-induced edema |
| 1 | 40.1 | 38.8 |
| 5 | 20.6 | — |
| 6 | 22.0 | — |
| 8 | 56.1 | 64.9 |
| 9 | 52.4 | 61.2[a] |
| 10 | 43.1 | 53.0 |
| 11 | 56.4 | 55.5[a] |
| 12 | 48.5 | 69.7[a] |
| 13 | 58.1 | 65.1 |
| 14 | 44.0 | 53.7[a] |
| 15 | 5.2 | 25.7[a] |
| 16 | 3.5 | N. T |
| 17 | 10.8 | N. T |
| 18 | 23.7 | 26.7[a] |
| 19 | 1.7 | N. T |
| 20 | 6.8 | N. T |
| 21 | 2.3 | N. T |
| 22 | 1.9 | 0 |
| 23 | 0 | 18.1[a] |
| 24 | 0.3[b] | N. T |
| 25 | 13.8 | N. T |
| 26 | 15.2 | N. T |
| 27 | 8.6 | N. T |
| 28 | 20.6 | 26.7[a] |
| 29 | 56.1 | 21.1[a] |
| 30 | 48.5 | 33.5[a] |
| 31 | 60.6 | 57.4[a] |
| 33 | 67.8[b] | 67.3[a] |
| 34 | 42.2[b] | 41.6[a] |
| 37 | 34.7[b] | 49.8[a] |
| 40 | 21.3 | 42.8[a] |
| 41 | 47.7 | 33.3[a] |
| 42 | 35.9 | 45.6[a] |
| 43 | 39.2 | 56.2[a] |
| 44 | 42.8 | 63.9[a] |
| 45 | 37.8 | 66.9[a] |
| 46 | N. T | 43.5[a] |
| 47 | 33.1 | 35.7[a] |
| 58 | 36.3[b] | 47.0[a] |
| 59 | 36.4[b] | 47.9[a] |

[a]: 25 mg/kg P.O.
[b]: 50 mg/kg P.O.

c) Effect on Type III allergic reaction-induced pleurisy

1. Preparation of IgG fraction of rabbit anti-egg white albumin (anti-OA)

IgG was purified from rabbit anti-OA serum prepared in advance by the method of Koda et al. [Folia Pharmacol., Japon 66, 237, (1970)] in the following manner.

A saturated solution of ammonium sulfate (half volume of the serum) was added to the anti-OA serum, and the mixture was left for one hour at 4° C. The precipitate was taken by centrifugation (3,000 rpm, 30 min. 4° C.) and dissolved in phosphate buffer of Dulbecco. Then, ammonium sulfate fractionation was carried out three times in the same manner as above, whereby a purified IgG fraction was obtained.

2. Type III allergic reaction-induced pleurisy

Male Wistar rats weighing 225–250 g were pre-bred for several days and fasted overnight prior to the experiment. The test compound (100 mg/kg) was orally administered to the animals, and after 30 minutes, a solution of IgC of rabbit anti-OA (0.2 ml, 5 mg protein/ml) was injected into the pleural cavity of the animals from the right side of thorax under anesthesia with ether. Thirty minutes after the injection of IgG, OA (albumin egg grade III; Sigma Chemical Co.) was intravenously injected into the animals as an inducer of pleurisy. After two hours, Evans Blue (25 mg/kg) was intravenously injected, and four and a half hours after the induction of pleurisy, the animals were killed by bleeding.

Then, an exudate in the pleural cavity was obtained, and the volume of the exudate was measured. The pleural cavity was rinsed with 5 ml of physiological saline and the rinsings were added to the exudate. The number of infiltrated cells in the mixture was counted and the volume of the dye in the mixture was determined by the absorption at 625 nm [Agent Actions., 25, 326 (1988)]. The suppression rates for the volume of the exudate, the number of infiltrated cells and the volume of the dye in the pleural cavity were calculated by the following equation 3.

$$\text{Suppression rate (\%)} = 100 - \frac{S.V - N.V}{P.V - N.V} \times 100 \quad (3)$$

S.V: the value obtained with the group administered with the test compound and in which pleurisy is induced N.V: the value obtained with the group in which pleurisy is not induced P.V: the value obtained with the group administered with no test compound and in which pleurisy is induced The results are shown in Table 3.

TABLE 3

| Compound | Suppression rate (%) | | |
|---|---|---|---|
| | Volume of exudate | Volume of dye in the exudate | Number of infiltrated cells in the exudate |
| 1 | 100 | 80.3 | 84.1 | d) Effect on passive Schultz-Dale reaction (bronchodilative activity)

Male Hartley guinea pigs weighing 350 to 500 g were passively sensitized by intraperitoneal injection of rabbit anti-OA serum prepared in advance by the method of Koda et al. [Folia Pharmacol., Japon 66, 237, (1970)]. After 24 hours, the guinea pigs were stunned and exsanguinated, and then tracheae were removed. The zig-zag strips of the tracheae were prepared by the method of Emmerson and Mackay [J. Pharm. Pharmacol., 31, 798, (1979)]. The strips were suspended in Krebs-Henseleit solution at 37° C. under aeration of a mixed gas of 95% oxygen and 5% carbon dioxide, and equilibrated for one hour. Then, antigen (egg white albumin) was introduced in the solution (final concentration; 1 μg/ml), and the contraction was measured by isotonictransducer (TD-112s, made by Nihon Kohden K.K., Japan) and recorded on a recorder (Type 3066, made by Yokogawa-Hokushin Denki, K.K. Japan). After the contraction curves reached a plateau, the test compounds were successively added in order to get cumulative concentration-relaxation curves. The concentration of 50% relaxation rate ($IC_{50}$) was calculated from the regression line, which was obtained from the cumulative concentration-relaxation curves.

The results are shown in Table 4.

TABLE 4

| Compound | Passive Schultz-Dale reaction ($IC_{50}$; μM) |
|---|---|
| 1 | 12 |
| 3 | 0.77 |
| 4 | 0.24 |
| 5 | >10 |
| 6 | >10 |
| 7 | >10 |
| 8 | 0.45 |
| 9 | 6.5 |
| 10 | 6.0 |
| 11 | >10 |
| 12 | 8.5 |
| 13 | 1.3 |
| 14 | 5.8 |
| 15 | 8.1 |
| 16 | >10 |
| 17 | >10 |
| 18 | >10 |
| 19 | >10 |
| 20 | >10 |
| 21 | 2.0 |
| 22 | >10 |
| 23 | >10 |
| 24 | >10 |
| 25 | >10 |
| 26 | >10 |
| 27 | >10 |
| 28 | 4.5 |
| 29 | 0.29 |
| 31 | 0.13 |
| 32 | 0.68 |
| 33 | 0.0071 |
| 34 | 0.68 |
| 37 | 6.2 |

TABLE 4-continued

| Compound | Passive Schultz-Dale reaction ($IC_{50}$; μM) |
|---|---|
| 41 | 10 |
| 44 | 6.6 |
| 48 | 4.9 | e) Inhibition effect on platelet activating factor (PAF)-induced mortality

The experiment was carried out by a minor modification of a known method [Br. J. Pharmacol., 79, 595 (1983)]. Groups each consisting of 10 male dd mice (weighing 28 to 32 g) were used, and 50 or 100 mg/kg of the test compound or a saline (control) was orally administered. One hour after the administration of test compound, 40 μg/kg of PAF (manufactured by Avanti Polar Lipids Co., Ltd.) was intravenously administered. Three hours after PAF injection, the mortality of the animals was observed. The compound whose mortality was significantly (Fischer's accurate probability tests) lower than control is regarded as having inhibitory effect on PAF-induced mortality, and the results are shown in Table 5 as survival rate.

TABLE 5

| Compound | Survival rate of control group | Survival rate of test compound-administered group |
|---|---|---|
| 1 | 20% | 90%*** |
| 3 | 0% | 70%** |
| 5 | 0% | 80%*** |
| 6 | 10% | 70%** |
| 7 | 20% | 90%** |
| 8 | 0% | 70%** |
| 9 | 0% | 100%*** |
| 10 | 0% | 80%*** |
| 11 | 0% | 100%*** |
| 12 | 0% | 100%*** |
| 13 | 10% | 90%*** |
| 14 | 0% | 100%*** |
| 15 | 10% | 50% |
| 16 | 0% | 0% |
| 17 | 0% | 30% |
| 18 | 10% | 90%*** |
| 19 | 10% | 60% |
| 20 | 10% | 30% |
| 21 | 10% | 30% |
| 22 | 0% | 30% |
| 23 | 0% | 10% |
| 24 | 10% | 40% |
| 25 | 10% | 60% |
| 26 | 10% | 90%*** |
| 27 | 0% | 60%** |
| 28 | 0% | 70%** |
| 29 | 0% | 100%*** |
| 30 | 0% | 90%*** |
| 31 | 0% | 90%*** |
| 32 | 0% | 0% |
| 33 | 0% | 100%*** |
| 34 | 0% | 70%** |
| 35 | 10% | 70%** |
| 36 | 10% | 20% |
| 37 | 10% | 90%*** |
| 38 | 10% | 30% |
| 39 | 0% | 0% |
| 40 | 0% | 40% |
| 41 | 0% | 80%***a |
| 42 | 0% | 100%***a |
| 43 | 0% | 70%** |
| 44 | 0% | 50% |
| 45 | 0% | 40% |
| 46 | 0% | 10% |
| 47 | 0% | 0% |

TABLE 5-continued

| Compound | Survival rate of control group | Survival rate of test compound-administered group |
|---|---|---|
| 48 | 0% | 10% |
| 49 | 0% | 0% |
| 50 | 0% | 0% |
| 51 | 0% | 80%*** |
| 52 | 0% | 100%*** |
| 53 | 0% | 90%*** |
| 54 | 0% | 90%*** |
| 55 | 0% | 0% |
| 56 | 10% | 40% |
| 57 | 0% | 0% |
| 58 | 0% | 100%*** |
| 59 | 10% | 70%** |
| 60 | 0% | 20% |
| 61 | 0% | 10% |
| 62 | 10% | 90%*** |
| 64 | 10% | 60% |
| 66 Sa | 0% | 70%** |
| 67 Sa | 10% | 30% |

[a]: 50 mg/kg p.o.
[**]: $p < 0.01$,
[***]: $p < 0.001$ n = 10
Sa: hydrochloride of the compound f) Acute toxicity The test compound was orally and intraperitoneally administered to ddY strain male mice weighing 20 to 25 g. MLD (Minimum Lethal Dose) was determined by observing the mortality for days after the administration.

The results are shown in Table 6.

TABLE 6

| Compound | MLD (mg/kg) | |
|---|---|---|
| | p.o. | i.p. |
| 2 | >300 | >100 |
| 3 | >300 | >100 |
| 4 | >50 | >50 |
| 8 | >50 | >50 |
| 9 | >100 | >100 |
| 10 | >100 | >100 |
| 11 | >200 | >100 |
| 12 | >200 | >50 |
| 13 | >300 | >100 |
| 14 | >100 | >100 |
| 15 | >300 | >100 |
| 16 | >300 | >100 |
| 17 | >300 | >100 |
| 21 | >300 | >100 |
| 29 | >100 | >100 |
| 30 | >300 | >100 |
| 31 | >300 | >100 |
| 32 | >300 | >100 |
| 33 | >300 | >100 |
| 34 | >300 | >100 |
| 35 | >300 | >100 |
| 36 | >300 | >100 |
| 43 | >300 | >100 |
| 44 | >300 | >50 |
| 47 | >300 | >100 |
| 58 | >300 | >100 |
| 59 | >300 | >100 |
| 66 Sa | >300 | >100 |
| 67 Sa | >300 | >100 |

Sa: hydrochloride of the compound

Compounds (I) and pharmaceutically acceptable salts thereof may be used as they are or in various preparation forms. The pharmaceutical composition of the present invention can be prepared by uniformly mixing Compound (I) or a pharmaceutically acceptable salt thereof as the active ingredient in an effective amount, with pharmaceutically acceptable carriers. These pharmaceutical compositions are desirably in a single dose unit which is suited for oral or parenteral administration.

In preparing the composition for oral administration, any pharmaceutically acceptable carriers may be used according to the preparation form. For example, liquid preparations such as a suspension and a syrup may be prepared using water; sugars such as sucrose, sorbitol and fructose; glycols such as polyethylene glycol and propylene glycol; oils such as sesame oil, olive oil and soybean oil; preservatives such as p-hydroxybenzoic acid esters; flavors such as strawberry flavor and peppermint, etc. Powders, pills, capsules and tablets may be prepared using excipients such as lactose, glucose, sucrose and mannitol; disintegrators such as starch and sodium alginate; lubricants such as magnesium stearate and talc; binders such as polyvinyl alcohol, hydroxypropyl cellulose and gelatin; surfactants such as fatty acid esters; plasticizers such as glycerine, etc. Tablets and capsules are the most useful single dose units for oral administration since their administration is easy. In preparing tablets and capsules, solid pharmaceutical carriers are used.

A solution for parenteral administration may be prepared using carriers such as distilled water, a saline solution, a glucose solution, and a mixture of a saline solution and a glucose solution.

The effective dose and the administration schedule of Compounds (I) or pharmaceutically acceptable salts thereof vary depending upon mode of administration, age, body weight and conditions of a patient, etc., but it is generally preferred to administer the effective compound in a dose of 1 to 1,000 mg/person/day at one time or in 2 to 4 parts.

Furthermore, Compounds (I) may be administered by inhalation in the form of aerosol, finely pulverized powders, or spray solution. In the case of aerosol administration, the present compounds are dissolved in an appropriate pharmaceutically acceptable solvent, for example, ethyl alcohol or a combination of miscible solvents, and then mixed with a pharmaceutically acceptable propellant.

Certain embodiments of the present invention are illustrated in the following examples.

EXAMPLE 1

5-(n-Butyl)-1-methyl-1H-imidazo[4,5-c][1,8] naphthyridin-4(5H)-one (Compound 1)

In 100 ml of ethanol was suspended 2.0 g (7.7 mmol) of Compound e obtained in Reference Example 5, and 0.40 g of 10% palladium/carbon was added to the suspension. Hydrogen gas was bubbled into the mixture at room temperature for 2 hours. After the catalyst was removed by filtration, the solvent was distilled off under reduced pressure. To the resulting residue was added 12.8 ml (77.5 mmol) of ethyl orthoformate, and the mixture was stirred at 130° C. for 30 minutes. The resulting solution was cooled to room temperature and filtered to obtain crystals. Recrystallization from isopropanol-isopropyl ether gave 1.0 g (yield 51%) of Compound 1 as white crystals.

Melting point: 198.5°–202° C.

Elemental analysis (%): $C_{14}H_{16}N_4O$ Calcd.: C 65.61, H 6.29, N 21.86 Found: C 65.50, H 6.49, N 22.09

IR(KBr) vmax(cm$^{-1}$): 1665, 1547, 1379

$^1$H-NMR(CDCl$_3$) δ (ppm): 8.58(1H, dd, J=4, 2 Hz), 8.26 (1H, dd, J=8, 2 Hz), 7.76(1H, s), 7.22(1H, dd, J=8, 4 Hz), 4.60(2H, t, J=7 Hz), 4.16(3H, s), 1.65–1.80(2H, m), 1.37–1.53(2H, m), 0.95(3H, t, J=7 Hz)

MS m/e: 256(M⁺), 214, 200

EXAMPLE 2

1-Methyl-5-phenyl-1H-imidazo[4,5-c][1,8]naphthyridin-4(5H)-one (Compound 2)

Compound b obtained in Reference Example 2 (1.2 g, 4.0 mmol) was suspended in a solvent mixture of 10 ml of ethanol and 10 ml of water, and 2.8 g (16 mmol) of sodium hydrosulfite was added to the suspension. After stirring in an oil bath at 100° C. for 10 minutes, the resulting solution was cooled and then filtered. The obtained crystals were washed with water and dried, followed by addition of 8.0 ml (48 mmol) of ethyl orthoformate. The mixture was stirred at 130° C. for one hour. The resulting solution was cooled and 30 ml of isopropyl ether was added thereto. Crude crystals were collected by filtration. Recrystalllization from isopropanol-isopropyl ether gave 0.64 g (yield 58%) of Compound 2 as white crystals.

Melting point: 262° C. (carbonized)

Elemental analysis (%): $C_{16}H_{12}N_4O$ Calcd.: C 69.55, H 4.38, N 20.28 Found: C 69.68, H 4.27, N 20.19

IR(KBr) vmax(cm⁻¹): 1667, 1575, 1550

¹H-NMR($d_6$-DMSO) δ (ppm): 8.60(1H, dd, J=8, 2 Hz), 8.35 (1H, dd, J=4, 2 Hz), 8.20(1H, s), 7.41–7.57(3H, m), 7.34(1H, dd, J=8, 4 Hz), 7.22–7.27(2H, m), 4.22 (3H, s)

MS m/e: 276 (M⁺), 275

EXAMPLE 3

5-Phenyl-3H-imidazo[4,5-c][1,8]naphthyridin-4(5H)-one (Compound 3)

Compound 3 was obtained as colorless crystals (yield 58%) according to the same procedure as in Example 2 except that Compound c obtained in Reference Example 3 was used instead of Compound b and the recrystallization was carried out from dimethylformamide-water.

Melting point: >300° C.

Elemental analysis (%): $C_{15}H_{10}N_4O \cdot 0.2H_2O$ Calcd.: C 67.76, H 3.94, N 21.07 Found: C 67.92, H 3.45, N 21.10

IR(KBr) vmax(cm⁻¹): 1668, 1583, 1423

¹H-NMR($d_6$-DMSO) δ (ppm): 13.84(1H, br.s), 8.50(1H, dd, J=8, 2 Hz), 8.33–8.36 (2H, m), 7.42–7.58(3H, m), 7.22–7.38 (3H, m)

MS m/e: 262(M⁺), 261

EXAMPLE 4

3-Methyl-5-phenyl-3H-imidazo[4,5-c][1,8]naphthyridin-4(5H)-one (Compound 4)

In 3 0 ml of dimethylformamide was dissolved 0.80 g (3.1 mmol) of Compound 3 obtained in Example 3, and 0.18 g (4.6 mmol) of 60% sodium hydride in oil was added to the solution at room temperature. After evolution of hydrogen ceased, 0.40 ml (6.3 mmol) of methyl iodide was added to the reaction mixture, followed by stirring for 5 hours. Then, 2 ml of a saturated aqueous solution of ammonium chloride was added to the mixture, and the solvent was distilled off under reduced pressure. The resulting residue was subjected to silica gel column chromatography (developing solvent: chloroform/methanol=70/1) to obtain crystals. Recrystallization from ethanol-isopropyl ether gave 0.61 g (yield 72%) of Compound 4 as colorless crystals.

Melting point: >300° C.

Elemental analysis (%): $C_{16}H_{12}N_4O$ Calcd.: C 69.55, H 4.38, N 20.28 Found: C 6 9.85, H 4.10, N 20.28

IR(KBr) vmax (cm⁻¹): 1663, 1574

¹H-NMR($d_6$-DMSO) δ (ppm): 8.50(1H, dd, J=8, 2 Hz), 8.34 (1H, s), 8.34(1H, dd, J=4, 2 Hz), 7.42–7.57 (3H, m), 7.27–7.36(3H, m), 4.06(3H, s)

MS m/e: 276(M⁺), 275

EXAMPLE 5

1-Ethyl-5-phenyl-1H-imidazo[4,5-c][1,8]naphthyridin-4(5H)-one (Compound 5)

Compound 5 was obtained according to the same procedure as in Example 3 except that Compound h obtained in Reference Example 6 was used instead of Compound c (yield 24%).

Melting point (solvent for recrystallization): >300° C. (methanol)

Elemental analysis (%): $C_{17}H_{14}N_4O$ Calcd.: C 70.33, H 4.81, N 19 33 Found: C 70.33, H 4.86, N 19.30

IR(KBr) vmax(cm⁻¹): 1666, 1378, 712

¹H-NMR($d_6$-DMSO) δ (ppm): 8.52(1H, dd, J=8, 2 Hz), 8.36 (1H, dd, J=4, 2 Hz), 8.27(1H, s), 7.40–7.60(4H, m), 7.37(1H, dd, J=8, 4 Hz), 7.21–7.29(2H, m), 4.67 (2H, q, J=7 Hz), 1.51(3H, t, J=7 Hz)

MS m/e: 290 (M⁺), 289

EXAMPLE 6

1-Isopropyl-5-phenyl-1H-imidazo[4,5-c][1,8]naphthyridin-4 (5H)-one (Compound 6)

Compound 6 was obtained according to the same procedure as in Example 3 except that Compound i obtained in Reference Example 7 was used instead of Compound c (yield 56%).

Melting point (solvent for recrystallization): >300° C. (ethanol)

Elemental analysis (%): $C_{18}H_{16}N_4O$ Calcd.: C 71.02, H 5.23, N 18.16 Found: C 71.04, H 5.30, N 18.41

IR (KBr) vmax (cm⁻¹): 1664

H-NMR($d_6$-DMSO) δ (ppm): 8.58(1H, dd, J=8, 2 Hz), 8.44 (1H, s), 8.35(1H, dd, J=4, 2 Hz), 7.41–7.57(4H, m), 7.36(1H, dd, J=8, 4 Hz), 7.22–7.28(2H, m)

MS m/e: 304(M⁺), 303, 261

EXAMPLE 7

1-Benzyl-5-phenyl-1H-imidazo[4,5-c][1,8]naphthyridin-4(5H)-one (Compound 7)

Compound 7 was obtained according to the same procedure as in Example 3 except that Compound j obtained in Reference Example 8 was used instead of Compound c (yield 15%).

Melting point (solvent for recrystallization): >300° C. (ethanol)

Elemental analysis (%): $C_{22}H_{16}N_4O$ Calcd.: C 74.59, H 4.58, N 16.20 Found: C 74.98, H 4.58, N 15.90

IR(KBr) vmax(cm⁻¹): 1661

¹H-NMR ($d_6$-DMSO) δ (ppm): 8.42(1H, s), 8.27(1H, dd, J= 4, 2 Hz), 8.24(1H, dd, J=8, 2 Hz), 7.15–7.57(11H, m), 5.95(2H, s)

MS m/e: 352(M$^+$), 351, 91

In Examples 8–16, the same procedure as in Example 4 was repeated except that the compounds shown in Table 7 were used respectively instead of methyl iodide.

EXAMPLE 8

3-Ethyl-5-phenyl-3H-imidazo[4,5-c][1,8]naphthyridin-4(5H)-one (Compound 8)

Melting point (solvent for recrystallization): 233°–234° C. (chloroform-isopropyl ether)

Elemental analysis (%): $C_{17}H_{14}N_4O$ Calcd.: C 70.58, H 4.82, N 19.50 Found: C 70.33, H 4.86, N 19.29

IR (KBr) vmax (cm$^{-1}$): 1661

$^1$H-NMR (d$_6$-DMSO) δ (ppm): 8.53(1H, dd, J=8, 2 Hz), 8.43 (1H, s), 8.36(1H, dd, J=4, 2 Hz), 7.27–7.58 (6H, m), 4.50(2H, q, J=7 Hz), 1.44(3H, t, J=7 Hz)

MS m/e: 290(M$^+$), 289

EXAMPLE 9

5-Phenyl-3-n-propyl-3H-imidazo[4,5-c][1,8]naphthyridin-4(5H)-one (Compound 9)

Melting point (solvent for recrystallization): 194°–204° C. (ethyl acetate-n-hexane)

Elemental analysis (%): $C_{18}H_{16}N_4O$ Calcd.: C 71.10, H 5.37, N 18.75 Found: C 71.03, H 5.30, N 18.41

IR(KBr) vmax (cm$^{-1}$): 1661, 457

$^1$H-NMR (d$_6$-DMSO) δ (ppm): 8.52(1H, dd, J=8, 2 Hz), 8.42 (1H, s), 8.36(1H, dd, J=4, 2 Hz), 7.23–7.65(6H, m), 4.41(2H, t, J=7 Hz), 1.73–1.93(2H, m), 0.86(3H, t, J=7 Hz)

MS m/e: 304(M$^+$), 303, 261

EXAMPLE 10

3-Isopropyl-5-phenyl-3H-imidazo[4,5-c][1,8]naphthyridin-4 (5H)-one (Compound 10)

Melting point (solvent for recrystallization): 192°–193° C. (isopropanol-water)

Elemental analysis (%): $C_{18}H_{16}N_4O$ Calcd.: C 71.07, H 5.17, N 18.33 Found: C 71.03, H 5.30, N 18.41

IR(KBr) vmax(cm$^{-1}$): 1661, 732

$^1$H-NMR(d$_6$-DMSO) δ (ppm): 8.57(1H, s), 8.55(1H, dd, J=8, 2 Hz), 8.36(1H, dd, J=4, 2 Hz), 7.43–7.60(3H, m), 7.26–7.39(3H, m), 5.25–5.41(1H, m), 1.56(6H, d)

MS m/e: 304(M$^+$), 303, 261

EXAMPLE 11

3-n-Butyl-5-phenyl-3H-imidazo[4,5-c][1,8]naphthyridin-4(5H)-one (Compound 11)

Melting point (solvent for recrystallization): 192°–194° C. (ethyl acetate-isopropyl ether)

Elemental analysis (%): $C_{19}H_{18}N_4O$ Calcd.: C 71.55, H 5.73, N 17.67 Found: C 71.68, H 5.70, N 17.60

IR(KBr) vmax(cm$^{-1}$): 1667, 717

$^1$H-NMR (d$_6$-DMSO) δ (ppm): 8.52(1H, dd, J=8, 2 Hz), 8.42 (1H, s), 8.36(1H, dd, J=4, 2 Hz), 7.42–7.58(3H, m), 7.25–7.39(3H, m), 4.45(2H, t, J=7 Hz), 1.72–1.89 (2H, m), 1.21–1.39(2H, m), 0.89(3H, t, J=7 Hz)

MS m/e: 318(M$^+$), 317, 261

EXAMPLE 12

3-Isobutyl-5-phenyl-3H-imidazo[4,5-c][1,8]naphthyridin-4 (5H)-one (Compound 12)

Melting point (solvent for recrystallization): 255°–267° C. (isopropyl ether)

Elemental analysis (%): $C_{19}H_{18}N_4O \cdot 0.1H_2O$ Calcd.: C 71.15, H 5.62, N 17.46 Found: C 71.28, H 5.73, N 14.50

IR(KBr) vmax(cm$^{-1}$): 1671

$^1$H-NMR (d$_6$-DMSO) δ (ppm): 8.53(1H, dd, J=8, 2 Hz), 8.40 (1H, s), 8.36(1H, dd, J=4, 2 Hz), 7.26–7.60(6H, m), 4.26(2H, d, J=7 Hz), 2.10–2.25(1H, m), 0.86(6H, d, J=7 Hz)

MS m/e: 318(M$^+$), 317, 262

EXAMPLE 13

3-Benzyl-5-phenyl-3H-imidazo[4,5-c][1,8]naphthyridin-4(5H)-one (Compound 13)

Melting point (solvent for recrystallization): 188°–192° C. (ethanol-water)

Elemental analysis (%): $C_{22}H_{16}N_4O$ Calcd.: C 75.13, H 4.57, N 15.97 Found: C 74.98, H 4.57, N 15.59

IR(KBr) vmax(cm$^{-1}$): 1668, 1651

$^1$H-NMR(d$_6$-DMSO) δ (ppm): 8.59(1H, s), 8.53(1H, dd, J= 8, 2 Hz), 8.36(1H, dd, J=4, 2 Hz), 7.26–7.60(11H, m), 5.72(2H, s)

MS m/e: 352(M$^+$), 351, 91

EXAMPLE 14

3-(2-Oxopropyl)-5-phenyl-3H-imidazo[4,5-c][1,8]-naphthyridin-4(5H)-one (Compound 14)

Melting point (solvent for recrystallization): 275°–276° C. (ethyl acetate)

Elemental analysis (%): $C_{18}H_{14}N_4O_2$ Calcd.: C 67.75, H 4.23, N 17.38 Found: C 67.91, H 4.43, N 17.59

IR (KBr) vmax (cm$^{-1}$): 1661

$^1$H-NMR (d$_6$-DMSO) δ (ppm): 8.62(1H, dd, J=8, 2 Hz), 8.45 (1H, dd, J=4, 2 Hz), 7.90(1H, s), 7.47–7.65(3H, m), 7.25–7.35(3H, m), 5.38(2H, s), 2.32(3H, s)

MS m/e: 318(M$^+$), 317, 275

EXAMPLE 15

3-Phenethyl-5-phenyl-3H-imidazo[4,5-c][1,8]naphthyridin-4 (5H)-one (Compound 15)

Melting point (solvent for recrystallization): 232°–233° C. (isopropanol-ethanol-water)

Elemental analysis (%): $C_{23}H_{18}N_4O$ Calcd.: C 75.42, H 4.92, N 15.15 Found: C 75.39, H 4.95, N 15.29

IR(KBr) vmax (cm$^{-1}$): 1650

$^1$H-NMR(d$_6$-DMSO) δ (ppm): 8.58(1H, dd, J=8, 2 Hz), 8.45 (1H, dd, J=4, 2 Hz), 7.48–7.72(4H, m), 7.06–7.47 (8H, m), 4.72(2H, t, J=7 Hz), 3.21(2H, t, J=7 Hz)

MS m/e: 366(M$^+$), 261

EXAMPLE 16

3-(α-Methyl)benzyl-5-phenyl-3H-imidazo[4,5-c][1,8] naphthyridin-4(5H)-one (Compound 16)

Melting point (solvent for recrystallization): 221°–226° C. (chloroform-isopropyl ether)

Elemental analysis (%): $C_{23}H_{18}N_4O$ Calcd.: C 75.14, H 5.21, N 15.04 Found: C 75.39, H 4.95, N 15.29

IR(KBr) vmax (cm$^{-1}$): 1661

$^1$H-NMR ($d_6$-DMSO) δ (ppm): 8.55(1H, dd, J=8, 2 Hz), 8.29–8.42(2H, m), 7.16–7.62(6H, m), 5.27(2H, s)

MS m/e: 360(M$^+$), 261

TABLE 7

| Compound | Compound used instead of methyl iodide | Yield (%) |
|---|---|---|
| 8 | CH$_3$CH$_2$I | 96 |
| 9 | CH$_3$CH$_2$CH$_2$I | 71 |
| 10 | (CH$_3$)$_2$CHI | 41 |
| 11 | CH$_3$CH$_2$CH$_2$CH$_2$I | 70 |
| 12 | (CH$_3$)$_2$CHCH$_2$Br | 71 |
| 13 | C$_6$H$_5$—CH$_2$Br | 78 |
| 14 | CH$_3$COCH$_2$Br | 60 |
| 15 | C$_6$H$_5$—CH$_2$CH$_2$Br | 75 |
| 16 | C$_6$H$_5$—CH(CH$_3$)Br | 75 |

EXAMPLE 17

3-Carboxymethyl-5-phenyl-3H-imidazo[4,5-c][1,8]-naphthyridin-4(5H)-one (Compound 17)

The same procedure as in Example 4 was repeated except that tert-butyl bromoacetate was used instead of methyl iodide, whereby 3-tert-butyloxycarbonylmethyl-5-phenyl-3H[4,5-c][1,8]naphthyridin-4(5H)-one (Compound 101) was obtained (yield 55%).

Compound 101(3.6 g) was dissolved in 180 ml of methylene chloride, and 80 ml of trifluoroacetic acid was added to the solution under ice cooling. The mixture was stirred at room temperature for 6 hours, and the solvent was distilled off under reduced pressure. The resulting residue was suspended in water and 4N aqueous solution of sodium hydroxide was added to dissolve the residue. Thereafter 2N hydrochloric acid was added to the solution to give the precipitate, which was collected by filtration. Recrystallization from dimethylformamide (hereinafter referred to as DMF)-water gave 1.4 g (yield 45%) of Compound 17 as white crystals.

Melting point (solvent for recrystallization): >300° C. (DMF-water)

Elemental analysis (%): $C_{17}H_{12}N_4O_3$ Calcd.: C 63.71, H 3.71, N 17.69 Found: C 63.74, H 3.77, N 17.49

IR(KBr) vmax(cm$^{-1}$): 1722, 1709, 1687, 1662

$^1$H-NMR($d_6$-DMSO) δ (ppm): 8.62(1H, dd, J=8, 2 Hz), 8.44 (1H, dd, J=4, 2 Hz), 8.00(1H, s), 7.17–7.70(11H, m), 6.70(1H, q, J=7 Hz), 1.98(3H, d, J=7 Hz)

MS m/e: 320(M$^+$), 319, 275

EXAMPLE 18

2-Methyl-5-phenyl-3H-imidazo[4,5-c][1,8]naphthyridin-4(5H)-one (Compound 18)

Compound c obtained in Reference Example 3 (12 g, 43 mmol) was suspended in 10 ml of ethanol and 14 ml of water, and 30 g (170 mmol) of sodium hydrosulfite was added to the suspension. After stirring in an oil bath at 100° C. for 10 minutes, the resulting solution was cooled and then filtered. The resulting crystals were dried to give 9.4 g (yield 88%) of 3,4-diamino-1-phenyl-1,8-naphthyridin-2(1H)-one (Compound 102) as a crude product.

Compound 102 (4.0 g, 16 mmol) was then suspended in 100 ml of methylene chloride, and 3.1 ml (22 mmol) of triethylamine and 1.4 ml (19 mmol) of acetyl chloride were successively added to the suspension under ice cooling with stirring. The mixture was stirred at room temperature for 1.5 hours.

Then, methanol was added to the mixture and the solvent was distilled off under reduced pressure. To the resulting residue were added 10 ml of dioxane and 10 ml of 2N sodium hydroxide solution, and the mixture was refluxed for 1.5 hours. The mixture was cooled with ice, and conc. hydrochloric acid was added thereto for neutralization. The formed crystals were taken by filtration. Recrystallization from methanol gave 2.0 g (yield 45%) of Compound 18 as colorless crystals.

Melting point (solvent for recrystallization): >300° C. (methanol)

Elemental analysis (%): $C_{16}H_{12}N_4O \cdot 0.5H_2O$ Calcd.: C 67.53, H 4.32, N 19.47 Found: C 67.36, H 4.59, N 19.63

IR(KBr) vmax(cm$^{-1}$): 1657, 730

$^1$H-NMR($d_6$-DMSO) δ (ppm): 13.5(1H, br.s), 8.57(1H, dd, J=8, 2 Hz), 8.33(1H, dd, J=4, 2 Hz), 7.18–7.61(6H, m), 2.51(3H, s)

MS m/e: 276(M$^+$), 275

EXAMPLE 19

2,5-Diphenyl-3H-imidazo[4,5-c][1,8]naphthyridin-4(5H)-one (Compound 19)

Compound 19 was obtained as colorless crystals according to the same procedure as in Example 18 except that benzoyl chloride was used instead of acetyl chloride (yield 73%).

Melting point (solvent for recrystallization): >300° C. (chloroform)

Elemental analysis (%): $C_{21}H_{14}N_4O$ Calcd.: C 74.50, H 4.05, N 16.49 Found: C 74.54, H 4.17, N 16.56

IR(KBr) vmax(cm$^{-1}$): 1651, 457

¹H-NMR(d₆-DMSO) δ (ppm): 8.29–8.41(3H, m), 7.27–7.72 (10H, m)

MS m/e: 338(M⁺), 337

EXAMPLE 20

2-Mercapto-5-phenyl-3H-imidazo[4,5-c][1,8]naphthyridin-4 (5H)-one (Compound 20)

Compound c obtained in Reference Example 3 (12 g, 43 mmol) was suspended in 10 ml of ethanol and 14 ml of water, and 30 g (170 mmol) of sodium hydrosulfite was added to the suspension. After stirring in an oil bath at 100° C. for 10 minutes, the solution was cooled and the resulting precipitate was collected by filtration. The obtained crystals were dried to give 9.4 g (yield 88%) of 3,4-diamino-1-phenyl-1,8-naphthyridin-2(1H)-one (Compound 102) as a crude product.

Compound 102 (2.0 g, 7.9 mmol) was then suspended in 80 ml of tetrahydrofuran, and 2.3 g (13 mmol) of thiocarbonyldiimidazole was added to the suspension. The mixture was heated to reflux for 2 hours. The solvent was distilled off under reduced pressure, and the residue was triturated with ethanol. The formed crystals were taken by filtration. Recrystallization from DMF gave 1.1 g (yield 47%) of Compound 20 as colorless crystals.

Melting point (solvent for recrystallization): >300° C. (DMF)

Elemental analysis (%): $C_{15}H_{10}N_4OS \cdot 0.1H_2O$ Calcd.: C 60.74, H 3.33, N 19.14 Found: C 60.84, H 3.47, N 18.92

IR(KBr) vmax(cm⁻¹): 1689, 1680

¹H-NMR(CF₃CO₂D) δ (ppm): 9.21(1H, dd, J=6, 1 Hz), 8.62 (1H, dd, J=4, 1 Hz), 8.02(1H, dd, J=6, 4 Hz), 7.76–7.95(3H, m), 7.49–7.62(2H, m)

MS m/e: 294 (M⁺), 293, 44

EXAMPLE 21

2-Hydroxy-5-phenyl-3H-imidazo[4,5-c][1,8]naphthyridin-4(5H)-one (Compound 21)

Compound 21 was obtained as colorless crystals according to the same procedure as in Example 20 except that carbonyldiimidazole was used instead of thiocarbonyldiimidazole (yield 45%).

Melting point (solvent for recrystallization): >300° C. (DMF)

Elemental analysis (%): $C_{15}H_{10}N_4O_2 \cdot 0.7H_2O$ Calcd.: C 61.72, H 3.56, N 19.18 Found: C 61.93, H 3.95, N 19.26

IR(KBr) vmax(cm⁻¹): 1722, 1649, 1628

¹H-NMR(d₆-DMSO) δ (ppm): 9.27(1H, dd, J=6, 1 Hz), 8.62 (1H, dd, J=4, 1 Hz), 7.98(1H, dd, J=6, 4 Hz), 7.76–7.95(3H, m), 7.47–7.63(2H, m)

MS m/e: 278(M⁺), 277, 194

In Examples 22–26, the same procedure as in Example 3 was repeated except that the compounds shown in Table 8 were used respectively instead of Compound c.

EXAMPLE 22

5-(4-Methoxy)phenyl-3H-imidazo[4,5-c][1,8]naphthyridin-4(5H)-one (Compound 22)

Melting point (solvent for recrystallization): >300° C. (DMF-water)

Elemental analysis (%): $C_{16}H_{12}N_4O_2$ Calcd.: C 65.64, H 4.04, N 19.25 Found: C 65.75, H 4.14, N 19.17

IR(KBr) vmax(cm⁻¹): 1668

EXAMPLE 23

5-(3-Methoxy)phenyl-3H-imidazo[4,5-c][1,8]naphthyridin-4(5H)-one (Compound 23)

Melting point (solvent for recrystallization): >300° C. (DMF-water)

Elemental analysis (%): $C_{16}H_{12}N_4O$ Calcd.: C 65.70, H 4.02, N 19.32 Found: C 65.75, H 4.14, N 19.17

IR(KBr) vmax(cm⁻¹): 1667

EXAMPLE 24

5-(4-Methyl)phenyl-3H-imidazo[4,5-c][1,8]naphthyridin-4(5H)-one (Compound 24)

Melting point (solvent for recrystallization): >300° C. (DMF-water)

Elemental analysis (%): $C_{16}H_{12}N_4O$ Calcd.: C 69.62, H 4.16, N 19.96 Found: C 69.55, H 4.38, 20.28

IR(KBr) vmax(cm⁻¹): 1665

EXAMPLE 25

5-(3-Methyl)phenyl-3H-imidazo[4,5-c][1,8]naphthyridin-4(5H)-one (Compound 25)

Melting point (solvent for recrystallization): >300° C. (DMF-water)

Elemental analysis (%): $C_{16}H_{12}N_4O$ Calcd.: C 69.83, H 4.58, N 19.96 Found: C 69.55, H 4.38, N 20.28

IR(KBr) vmax(cm⁻¹): 1667

EXAMPLE 26

5-(3-Chloro)phenyl-3H-imidazo[4,5-c][1,8]naphthyridin-4(5H)-one (Compound 26)

Melting point (solvent for recrystallization): >300° C. (DMF-water)

Elemental analysis (%): $C_{15}H_9ClN_4O$ Calcd.: C 60.33, H 2.81, N 19.06 Found: C 60.72, H 3.06, N 18.88.

IR(KBr) vmax (cm⁻¹): 1668

TABLE 8

| Compound | Starting Compound (Reference Example No.) | Yield (%) |
| --- | --- | --- |
| 22 | n - 1 (20) | 54 |
| 23 | n - 2 (21) | 50 |
| 24 | n - 3 (22) | 52 |
| 25 | n - 4 (23) | 37 |
| 26 | n - 5 (24) | 47 |

EXAMPLE 27

5-n-Butyl-3H-imidazo[4,5-c][1,8]naphthyridin-4(5H)-one (Compound 27)

Compound 27 was obtained according to the same procedure as in Example 3 except that Compound k obtained in Reference Example 9 was used instead of Compound c (yield 48%).

Melting point (solvent for recrystallization): >300° C. (DMF-water)

Elemental analysis (%): $C_{13}H_{14}N_4O$ Calcd.: C 64.24, H 5.80, N 22.97 Found: C 64.44, H 5.82, N 23.12

IR(KBr) vmax(cm$^{-1}$): 1664, 779

$^1$H-NMR($d_6$-DMSO) δ (ppm): 13.74(1H, br. s), 8.62(1H, dd, J=4, 2 Hz), 8.51(1H, dd, J=8, 2 Hz), 8.30(1H, br. s), 7.39(1H, dd, J=8, 4 Hz), 4.52(2H, t, J=7 Hz), 1.53–1.76(2H, m), 1.27–1.48(2H, m), 0.93 (3H, t, J=7 Hz)

MS m/e: 242 (M$^+$), 200, 186

EXAMPLE 28

5-n-Butyl-3-methyl-3H-imidazo[4,5-c][1,8]naphthyridin-4(5H)-one (Compound 28)

Compound 28 was obtained according to the same procedure as in Example 4 except that Compound 27 obtained in Example 27 was used instead of Compound 3 (yield 72%).

Melting point (solvent for recrystallization): 173°–174° C. (isopropyl ether)

Elemental analysis (%): $C_{14}H_{16}N_4O$ Calcd.: C 65.22, H 6.16, N 21.89 Found: C 65.61, H 6.29, N 21.86

IR(KBr) vmax(cm$^{-1}$): 1659, 776

$^1$H-NMR ($d_6$-DMSO) δ (ppm): 8.50(1H, dd, J=4, 2 Hz), 8.47 (1H, dd, (1H, dd, J=8, 2 Hz), 8.28(1H, s), 7.37(1H, dd, J=8, 4 Hz), 4.49(2H, t, J=7 Hz), 4.09(3H, s), 1.60–1.73(2H, m), 1.30–1.48(2H, m), 0.93(3H, t, J=7 Hz)

MS m/e: 256(M$^+$), 199, 200

EXAMPLE 29

5-n-Butyl-3-n-propyl-3H-imidazo[4,5-c][1,8]naphthyridin-4(5H)-one (Compound 29)

Compound 29 was obtained according to the same procedure as in Example 28 except that n-propyl iodide was used instead of methyl iodide (yield 82%).

Melting point (solvent for recrystallization): 87°–90° C. (n-hexane)

Elemental analysis (%): $C_{16}H_{20}N_4O$ Calcd.: C 67.58, H 7.16, N 19.87 Found: C 67.58, H 7.09, N 19.70

IR(KBr) vmax(cm$^{-1}$): 1661, 1369, 775

$^1$H-NMR ($d_6$-DMSO) δ (ppm): 8.62(1H, dd, J=4, 2 Hz), 8.50 (1H, dd, J=8, 2 Hz), 8.35(1H, s), 7.37(1H, dd, J=8, 4 Hz), 4.40–4.62(4H, m), 1.79–1.96(2H, m), 1.58–1.73(2H, m), 1.30–1.49(2H, m), 0.94(3H, t, J=7 Hz), 0.88(3H, t, J=7 Hz)

MS m/e: 284(M$^+$), 186

In Examples 30–54, the same procedure as in Example 4 was repeated except that the compounds shown in Table 9 were used respectively instead of methyl iodide.

EXAMPLE 30

3-Hexyl-5-phenyl-3H-imidazo[4,5-c][1,8]naphthyridin-4(5H)-one (Compound 30)

Melting point (solvent for recrystallization): 166°–168° C. (chloroform-isopropyl ether)

Elemental analysis (%): $C_{21}H_{22}N_4O$ Calcd.: C 72.85, H 6.48, N 16.32 Found: C 72.80, H 6.40, N 16.17

IR(KBr) vmax(cm$^{-1}$): 1673, 1574

$^1$H-NMR (CDCl$_3$) δ (ppm): 8.61(1H, dd, J=8, 2 Hz), 8.43 (1H, dd, J=4, 2 Hz), 7.95(1H, s), 7.46–7.68(3H, m), 7.20–7.45(3H, m), 4.50(2H, t, J=7 Hz), 1.80–2.11 (3H, m), 1.17–1.46(5H, m), 0.86(3H, t, J=7 Hz)

MS m/e: 346(M$^+$), 345, 261

EXAMPLE 31

3-(Ethoxyethyl)-5-phenyl-3H-imidazo[4,5-c][1,8]naphthyridin-4(5H)-one (Compound 31)

Melting point (solvent for recrystallization): 209°–210° C. (chloroform-isopropyl ether)

Elemental analysis (%): $C_{19}H_{18}N_4O_2$ Calcd.: C 68.25, H 5.43, N 16.76 Found: C 68.27, H 5.35, N 16.98

IR(KBr) vmax(cm$^{-1}$): 1661

$^1$H-NMR(CDCl$_3$) δ (ppm): 8.63(1H, dd, J=8, 2 Hz), 8.43 (1H, dd, J=4, 2 Hz), 8.08(1H, s), 7.43–7.66(3H, m), 7.17–7.37(3H, m), 4.72(2H, t, J=5 Hz), 3.79 (2H, t, J=5 Hz), 3.46(2H, q, J=7 Hz), 1.15(3H, t, J=7 Hz)

MS m/e: 334(M$^+$), 305, 289, 261

EXAMPLE 32

3-Ethoxycarbonylmethyl-5-phenyl-3H-imidazo[4,5-c][1,8]naphthyridin-4(5H)-one (Compound 32)

Melting point (solvent for recrystallization): 228°–229° C. (chloroform-isopropyl ether)

Elemental analysis (%): $C_9H_{16}N_4O_3$ Calcd.: C 65.50, H 4.62, N 16.08 Found: C 64.97, H 4.43, N 16.10

IR(KBr) vmax(cm$^{-1}$): 1730, 1672, 1241

$^1$H-NMR (CDCl$_3$) δ (ppm): 8.62(1H, dd, J=8, 2 Hz), 8.44 (1H, dd, J=4, 2 Hz), 8.00(1H, s), 7.46–7.65(3H, m), 7.18–7.38(5H, m), 5.33(2H, s), 4.25(2H, q, J=7 Hz), 1.27(3H, t, J=7 Hz)

MS m/e: 348(M$^+$), 347

EXAMPLE 33

3-(2-propenyl)-5-phenyl-3H-imidazo[4,5-c][1,8]-naphthyridin-4(5H)-one (Compound 33)

Melting point (solvent for recrystallization): 186°–189° C. (chloroform-isopropyl ether)

Elemental analysis (%): $C_{18}H_{14}N_4O$ Calcd.: C 71.50, H 4.66, N 18.53 Found: C 71.55, H 4.68, N 18.73

IR(KBr) vmax(cm$^{-1}$): 1665, 1573

$^1$H-NMR($d_6$-DMSO) δ (ppm): 8.53(1H, dd, J=8, 2 Hz), 8.41 (1H, s), 8.36(1H, dd, J=4, 2 Hz), 7.25–7.66(8H, m), 6.04–6.19(1H, m), 5.05–5.28(4H, m)

MS m/e: 302, 301(M$^+$)

EXAMPLE 34

3-(2-Acetoxyethyl)-5-phenyl-3H-imidazo[4,5-c][1,8] naphthyridin-4(5H)-one (Compound 34)

Melting point (solvent for recrystallization): 198° C. (ethyl acetate )

Elemental analysis (%): $C_{19}H_{16}N_4O_3$ Calcd.: C 65.51, H 4.63, N 16.68 Found: C 65.03, H 4.60, N 16.18

IR(KBr) vmax(cm$^{-1}$): 1741, 1667

$^1$H-NMR($d_6$-DMSO) δ (ppm): 8.53(1H, dd, J=8, 2 Hz), 8.43 (1H, s), 8.37(1H, dd, J=4, 2 Hz), 7.25–7.60(6H, m), 4.71(2H, t, J=5 Hz), 4.41(2H, t, J=5 Hz), 1.95 (3H, s)

MS m/e: 348(M$^+$), 347, 261

EXAMPLE 35

3-(1-Propylbutyl)-5-phenyl-3H-imidazo[4,5-c][1,8] naphthyridin-4(5H)-one (Compound 35)

Melting point (solvent for recrystallization ): 104°–10 5° C. (methanol-water)

IR(KBr) vmax(cm$^{-1}$): 2924, 1658

$^1$H-NMR (CDCl$_3$) δ (ppm): 8.62(1H, dd, J=8, 2 Hz), 8.42 (1H, dd, J=4, 2 Hz), 8.03(1H, s), 7.45–7.63(3H, m), 7.22–7.36(3H, m), 5.22–5.45(1H, m), 1.75–2.03 (4H, m), 1.10–1.42(4H, m), 0.89(6H, t, J=7 Hz)

MS m/e: 360(M$^+$), 261

EXAMPLE 36

3-Cinnamyl-5-phenyl-3H-imidazo[4,5-c][1,8] naphthyridin-4(5H)-one (Compound 36)

Melting point (solvent for recrystallization): 231°–233° C. (chloroform-isopropyl ether)

Elemental analysis (%): $C_{24}H_{18}N_4O \cdot 0.3H_2O$ Calcd.: C 75.10, H 4.88, N 14.60 Found: C 75.23, H 4.67, N 14.56

IR(KBr) vmax(cm$^{-1}$): 1665, 1571

$^1$H-NMR ($d_6$-DMSO) δ (ppm): 8.54(1H, dd, J=8, 2 Hz), 8.48 (1H, s), 8.36(1H, dd, J=4, 2 Hz), 7.20–7.58(11H, m), 7.50–7.67(2H, m), 7.25–7.33(2H, m)

MS m/e: 378, 117

EXAMPLE 37

3-Cyclohexylmethyl-5-phenyl-3H-imidazo[4,5-c][1,8]-naphthyridin-4(5H)-one (Compound 37)

Melting point (solvent for recrystallization): 236° C. (chloroform-n-hexane)

Elemental analysis (%): $C_{22}H_{22}N_4O$ Calcd.: C 73.71, H 6.18, N 15.63 Found: C 73.55, H 6.10, N 15.64

IR(KBr) vmax(cm$^{-1}$): 1678, 1573

$^1$H-NMR($d_6$-DMSO) δ (ppm): 8.51(1H, dd, J=8, 2 Hz), 8.37 (1H, s), 8.35(1H, dd, J=4, 2 Hz), 4.30(2H, d), 1.41–1.93(5H, m), 0.90–1.25(6H, m)

MS m/e: 358(M$^+$), 275, 261

EXAMPLE 38

3-(3-Diphenylmethyl)-5-phenyl-3H-imidazo-[4,5-c]-[1,8]naphthyridin-4(5H)-one (Compound 38)

Melting point (solvent for recrystallization): 109°–113° C. (chloroform-isopropyl ether)

IR(KBr) vmax(cm$^{-1}$): 3652, 1674, 1495

$^1$H-NMR (CDCl$_3$) δ (ppm): 8.61(1H, dd, J=8, 2 Hz), 8.42 (1H, dd, J=4, 2 Hz), 7.80(1H, s), 7.03–7.60(17H, m)

MS m/e: 428(M$^+$), 167

EXAMPLE 39

3-(2,5-Dimethylphenyl)methyl-5-phenyl-3H-imidazo-[4,5-c][ 1,8]naphthyridin-4(5H)-one (Compound 39)

Melting point (solvent for recrystallization): 237°–238° C. (DMF-methanol)

Elemental analysis (%): $C_{24}H_{20}N_4O$ Calcd.: C 75.77, H 5.30, N 14.73 Found: C 75.80, H 5.28, N 14.12

IR(KBr) vmax(cm$^{-1}$): 1674

$^1$H-NMR($d_6$-DMSO) δ (ppm): 8.56(1H, dd, J=8, 2 Hz), 8.35–8.42(2H, m), 7.24–7.53(6H, m), 6.96–7.12(4H, m), 6.61(1H, s), 5.71(2H, s), 2.28(3H, s), 2.16(3H, s)

MS m/e: 380(M$^+$), 379

EXAMPLE 40

3-(4-Chlorophenyl)methyl-5-phenyl-3H-imidazo[4,5-c]-[1,8]naphthyridin-4(5H)-one (Compound 40)

Melting point (solvent for recrystallization): 287°–290° C. (DMF-methanol)

Elemental analysis (%): $C_{22}H_{15}N_4OCl$ Calcd.: C 68.39, H 3.91, N 14.50 Found: C 68.41, H 3.62, N 14.48

IR(KBr) vmax(cm$^{-1}$): 1671, 1616

$^1$H-NMR($d_6$-DMSO) δ (ppm): 8.61(1H, s), 8.52(1H, dd, J=8, 2 Hz), 8.36(1H, dd, J=4, 2 Hz), 7.23–7.58 (10H, m), 5.70(2H, s)

MS m/e: 388, 387, 386(M$^+$), 385

EXAMPLE 41

3-(3-Methylphenyl)methyl-5-phenyl-3H-imidazo[4,5-c]-[1,8]naphthyridin-4(5H)-one (Compound 41)

Melting point: (solvent for recrystallization): 238°–239° C. (ethanol-methanol)

Elemental analysis (%): $C_{23}H_{18}N_4O$ Calcd.: C 75.39, H 4.95, N 15.29 Found: C 75.17, H 4.61, N 15.28

IR(KBr) vmax(cm$^{-1}$): 1665, 1575

$^1$H-NMR($d_6$-DMSO) δ (ppm): 8.58(1H, s), 8.52(1H, dd, J=8, 2 Hz), 8.36(1H, dd, J=4, 2 Hz), 7.06–7.56 (10H, m), 5.68(2H, s), 2.26(3H, s)

MS m/e: 366(M$^+$), 365

EXAMPLE 42

3-(4-Nitrophenyl)methyl-5-phenyl-3H-imidazo[4,5-c]-[1,8] naphthyridin-4(5H)-one (Compound 42)

Melting point (solvent for recrystallization): 256°–259° C. (DMF-methanol)

Elemental analysis (%): $C_{22}H_{15}N_5O_3$ Calcd.: C 63.61, H 4.12, N 16.86 Found: C 63.76, H 3.84, N 16.28

IR(KBr) vmax(cm$^{-1}$): 1663, 1576

$^1$H-NMR($d_6$-DMSO) δ (ppm): 8.65(1H, s), 8.54(1H, dd, J=8, 2H), 8.37(1H, dd, J=4, 2 Hz), 8.19(2H, 9 Hz), 7.17–7.61(8H, m), 5.85(2H, s)

MS m/e: 397(M$^+$), 396

EXAMPLE 43

3-(4-Methylphenyl)methyl-5-phenyl-3H-imidazo-[4,5-c][1,8] naphthyridin-4(5H)-one (Compound 43)

Melting point (solvent for recrystallization): 238°–243° C. (DMF-methanol)

Elemental analysis (%): $C_{23}H_{18}N_4O \cdot 0.8H_2O$ Calcd.: C 72.54, H 5.19, N 14.71 Found: C 72.47, H 5.05, N 14.20

IR(KBr) vmax(cm$^{-1}$): 1669, 1575

$^1$H-NMR(d$_6$-DMSO) δ (ppm): 8.57(1H, s), 8.51(1H, dd, J=8, 2 Hz), 8.35(1H, dd, J=4, 2 Hz), 7.05–7.58 (10H, m), 5.66(2H, s), 2.25(3H, s)

MS m/e: 366(M$^+$), 365, 105

EXAMPLE 44

3-(4-Fluorophenyl)methyl-5-phenyl-3H-imidazo-[4,5-c][1,8] naphthyridin-4(5H)-one (Compound 44)

Melting point (solvent for recrystallization): 253°–256° C. (DMF-methanol)

Elemental analysis (%): $C_{22}H_{15}N_4OF$ Calcd.: C 71.34, H 4.08, N 15.13 Found: C 71.08, H 3.68, N 14.83

IR(KBr) vmax(cm$^{-1}$): 1667, 1511

$^1$H-NMR(d$_6$-DMSO) δ (ppm): 8.61(1H, s), 8.51(1H, dd, J= 8, 2 Hz), 8.35(1H, dd, J=4, 2 Hz), 7.12–7.58(10H, m), 5.69(2H, s)

MS m/e: 370(M$^+$), 369

EXAMPLE 45

3-(4-Methoxyphenyl)methyl-5-phenyl-3H-imidazo-[4,5-c][1,8]naphthyridin-4(5H)- one (Compound 45)

Melting point (solvent for recrystallization): 267°–268° C (DMF-water)

Elemental analysis (%): $C_{23}H_{18}N_4O_2$ Calcd.: C 7 2.24, H 4.74, N 14.65 Found: C 7 2.11, H 4.32, N 14.63

IR(KBr) vmax(cm$^{-1}$): 1666, 1574

$^1$H-NMR (d$_6$-DMSO) δ (ppm): 8.57(1H, s), 8.50(1H, dd, J=8, 2 Hz), 8.35(1H, dd, J=4, 2 Hz), 8.23–8.56(8H, m), 6.88(2H, d, J=9 Hz), 5.63(2H, s), 3.70(3H, s)

MS m/e: 382(M$^+$), 381, 121

EXAMPLE 46

3-(3-Methoxyphenyl)methyl-5-phenyl-3H-imidazo-[4,5-c][1,8]naphthyridin-4(5H)- one (Compound 46)

Melting point (solvent for recrystallization): 209°–210° C. (DMF-water)

Elemental analysis (%): $C_{23}H_{18}N_4O_2$ Calcd.: C 72.24, H 4.74, N 14.65 Found: C 72.40, H 4.52, N 14.61

IR(KBr) vmax(cm$^{-1}$): 1667, 1574

$^1$H-NMR (d$_6$-DMSO) δ (ppm): 8.59(1H, s), 8.52(1H, dd, J=8, 2 Hz), 8.35(1H, dd, J=4, 2 Hz), 7.18–7.57 (7H, m), 6.82–6.98(3H, m), 5.68(2H, s), 3.71(3H, s)

MS m/e: 382(M$^+$), 381

EXAMPLE 47

3-(3-Nitrophenyl)methyl-5-phenyl-3H-imidazo[4,5-c]-[1,8]naphthyridin-4(5H)-one (Compound 47)

Melting point (solvent for recrystallization): 284°–289° C. (DMF-water)

Elemental analysis (%): $C_{22}H_{15}N_5O_3$ Calcd.: C 66.49, H 3.80, N 17.62 Found: C 66.42, H 3.45, N 17.67

IR(KBr) vmax(cm$^{-1}$): 1662, 1527

$^1$H-NMR(d$_6$-DMSO) δ (ppm): 8.68(1H, s), 8.52(1H, dd, J=8, 2 Hz), 8.36(1H, dd, J=4, 2 Hz), 8.25(1H, J=2 Hz), 8.11–8.16(1H, m), 7.73–7.82(1H, m), 7.23–7.67(7H, m), 5.84(2H, s)

MS m/e: 397(M$^+$), 396

EXAMPLE 48

3-(2-Chlorophenyl)methyl-5-phenyl-3H-imidazo-[4,5-c][1,8] naphthyridin-4(5H)-one (Compound 48)

Melting point (solvent for recrystallization): 257°–262° C. (DMF-water)

Elemental analysis (%): $C_{22}H_{15}N_4OCl$ Calcd.: C 6 8.39, H 3.91, N 14.50 Found: C 68.51, H 3.91, N 14.80

IR(KBr) vmax(cm$^{-1}$): 1664, 1557

$^1$H-NMR(d$_6$-DMSO) δ (ppm): 8.56(1H, dd, J=8, 2 Hz), 8.50 (1H, s), 8.38(1H, dd, J=4, 2 Hz), 7.15–7.57(9H, m), 6.86(1H, d, J=7 Hz), 5.83(2H, s)

MS m/e: 388, 387, 386(M$^+$), 385, 352, 351

EXAMPLE 49

3-(3-Bromophenyl)methyl-5-phenyl-3H-imidazo[4,5-c]-[1,8]naphthyridin-4(5H)-one (Compound 49)

Melting point (solvent for recrystallization): 244°–246° C. (DMF-water)

Elemental analysis (%): $C_{22}H_{15}N_4O$ Calcd.: C 61.27, H 3.51, N 12.99 Found: C 61.20, H 3.40, N 12.81

IR(KBr) vmax(cm$^{-1}$): 1666, 1575

$^1$H-NMR(d$_6$-DMSO) δ (ppm): 8.64(1H, s), 8.53(1H, dd, J=8, 2 Hz), 8.37(1H, dd, J=4, 2 Hz), 7.23–7.60(10H, m), 5.71(2H, s)

MS m/e: 432, 431, 430, 429(M$^+$)

EXAMPLE 50

3-(4-Methoxycarbonylphenyl)methyl-5-phenyl-3H-imidazo[4,5-c][1,8]naphthyridin-4(5H)-one (Compound 50)

Elemental analysis (%): C 24H$_{18}$N$_4$O$_3$ Calcd.: C 70.23, H 4.42, N 13.65 Found: C 70.65, H 4.43, N 13.55

$^1$H-NMR(d$_6$-DMSO) δ (ppm): 8.63(1H, s), 8.54(1H, dd, J=8, 2 Hz), 8.37(1H, dd, J=4, 2 Hz), 7.93(2H, d, J=12 Hz), 7.22–7.55(8H, m), 5.81(2H, s), 3.83(3H, s)

MS m/e: 410(M$^+$), 409

EXAMPLE 51

3-(3-Hydroxypropyl)-5-phenyl-3H-imidazo[4,5-c][1,8] naphthyridin-4(5H)-one (Compound 51)

Melting point (solvent for recrystallization): 248°–252° C. (chloroform-isopropyl ether)

Elemental analysis (%): $C_{18}H_{16}N_4O_2 \cdot 0.3H_2O$ Calcd.: C 66.37, H 5.14, N 17.20 Found: C 66.50, H 4.98, N 17.22

IR(KBr) vmax(cm$^{-1}$): 3676, 3650, 1587

$^1$H-NMR(d$_6$-DMSO) δ (ppm): 8.52(1H, dd, J=8, 2 Hz), 8.39 (1H, s), 8.35(1H, dd, J=4, 2 Hz), 7.23–7.58(6H, m), 4.51(2H, t, J=7 Hz), 3.41(2H, t, J=7 Hz), 1.92–2.04(2H, m)

MS m/e: 320(M$^+$), 319, 275

EXAMPLE 52

3-(2-Hydroxypropyl)-5-phenyl-3H-imidazo[4,5-c]-[1,8]naphthyridin-4(5H)-one (Compound 52)

Melting point (solvent for recrystallization): 95°–98° C. (chloroform-isopropyl ether)

Elemental analysis (%): $C_{18}H_{16}N_4O_2 \cdot 0.4H_2O$ Calcd.: C 66.00, H 5.17, N 17.10 Found: C 66.04, H 5.00, N 16.64

IR(KBr) vmax(cm$^{-1}$): 3676, 3630, 1662

$^1$H-NMR(d$_6$-DMSO) δ (ppm): 8.53(1H, dd, J=8, 2 Hz), 8.30–8.37(2H, m), 7.27–7.57(6H, m), 4.40–4.60 (2H, m), 3.78–3.92(1H, m), 3.45–3.70(1H, m), 1.10(3H, d, J=6 Hz)

MS m/e: 320, 319, 303, 261

EXAMPLE 53

3-Furfuryl-5-phenyl-3H-imidazo[4,5-c][1,8]naphthyridin-4(5H)-one (Compound 53)

Melting point (solvent for recrystallization): 252°–253° C. (chloroform-isopropyl ether)

Elemental analysis (%): $C_{20}H_{14}N_4O_2$ Calcd.: C 70.17, H 4.12, N 16.37 Found: C 70.10, H 3.98, N 16.25

$^1$H-NMR(d$_6$-DMSO) δ (ppm): 8.52(1H, dd, J=8, 2 Hz), 8.46 (1H, s), 8.36(1H, dd, J=4, 2 Hz), 7.61–7.63(1H, m), 7.42–7.56(3H, m), 7.27–7.38(3H, m), 6.41–6.47 (2H, m), 5.76(2H, s)

MS m/e: 342(M$^+$), 341, 81

EXAMPLE 54

5-Phenyl-3-(3-pyridyl)methyl-3H-imidazo[4,5-c][1,8]-naphthyridin-4(5H)-one (Compound 54)

Melting point (solvent for recrystallization): 273°–277° C. (chloroform-isopropyl ether)

Elemental analysis (%): $C_{21}H_{15}N_5OCl$ Calcd.: C 71.38, H 4.28, N 19.82 Found: C 71.43, H 4.19, N 19.74

IR(KBr) vmax(cm$^{-1}$): 2740, 1662

$^1$H-NMR(d$_6$-DMSO) δ (ppm): 8.64(2H, s), 8.45–8.53(2H, m) 8.36(1H, dd, J=4, 2 Hz), 7.76(1H, d, J=8 Hz), 7.26–7.60(8H, m), 5.76(2H, s)

MS m/e: 353(M$^+$), 352

TABLE 9

| Compound | Compound used instead of methyl iodide | Yield (%) |
|---|---|---|
| 30 | $CH_3CH_2CH_2CH_2CH_2CH_2I$ | 83 |
| 31 | $CH_3CH_2OCH_2CH_2Br$ | 95 |
| 32 | $CH_3CH_2OCCH_2Cl$ (C=O) | 77 |
| 33 | $CH_2=CHCH_2Br$ | 74 |

TABLE 9-continued

| Compound | Compound used instead of methyl iodide | Yield (%) |
|---|---|---|
| 34 | $CH_3COCH_2CH_2Br$ | 57 |
| 35 |  $(CH_3CH_2CH_2)_2CHOSO_2$—C$_6$H$_4$—$CH_3$ | 62 |
| 36 | 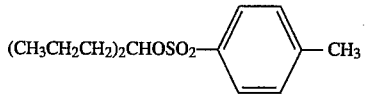 Ph—CH=CHCH$_2$Br | 81 |
| 37 | 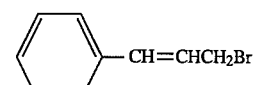 cyclohexyl—CH$_2$Br | 74 |
| 38 | 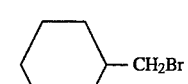 diphenylmethyl—CH$_2$Br | 54 |
| 39 | 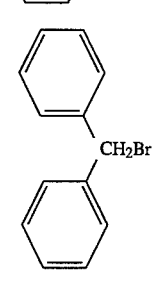 2,5-dimethylphenyl—CH$_2$Cl | 72 |
| 40 | 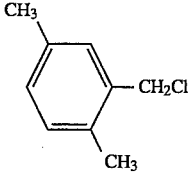 4-Cl-C$_6$H$_4$—CH$_2$Br | 93 |
| 41 | 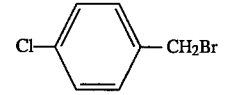 3-CH$_3$-C$_6$H$_4$—CH$_2$Br | 87 |
| 42 | 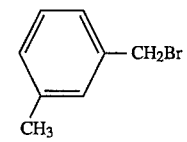 4-O$_2$N-C$_6$H$_4$—CH$_2$Cl | 98 |
| 43 | 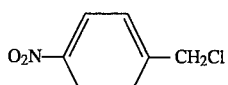 4-CH$_3$-C$_6$H$_4$—CH$_2$Br | 94 |
| 44 | 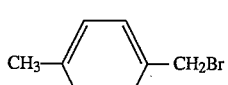 4-F-C$_6$H$_4$—CH$_2$Cl | 65 |

TABLE 9-continued

| Compound | Compound used instead of methyl iodide | Yield (%) |
|---|---|---|
| 45 | 4-CH3O-C6H4-CH2Cl | 56 |
| 46 | 3-CH3O-C6H4-CH2Cl | 76 |
| 47 | 3-NO2-C6H4-CH2Br | 78 |
| 48 | 2-Cl-C6H4-CH2Br | 75 |
| 49 | 3-Br-C6H4-CH2Br | 80 |
| 50 | 4-CH3O2C-C6H4-CH2Br | 51 |
| 51 | HOCH2CH2CH2Br | 30 |
| 52 | CH3CH(O)CH2 (propylene oxide) | 63 |
| 53 | furfuryl-CH2Cl | 59 |
| 54 | 3-pyridyl-CH2Cl | 68 |

In Examples 55–61, the same procedure as in Example 13 was repeated except that the compounds shown in Table 10 were used respectively instead of Compound 3.

EXAMPLE 55

5-(4-Methoxyphenyl)-3-benzyl-3H-imidazo[4,5-c]-[1,8]naphthyridin-4(5H)-one (Compound 55)

Melting point (solvent for recrystallization): 299° C. (chloroform-isopropyl ether)

Elemental analysis (%): $C_{23}H_{18}N_4O_2$ Calcd.: C 72.24, H 4.74, N 14.65 Found: C 72.51, H 4.80, N 14.41

IR(KBr) vmax(cm$^{-1}$): 1667

$^1$H-NMR($d_6$-DMSO) δ (ppm): 8.59(1H, s), 8.52(1H, dd, J=8, 2 Hz), 8.37(1H, dd, J=4, 2 Hz), 7.22–7.38(6H, m), 7.19(2H, dd, J=7, 2 Hz), 7.05(2H, dd, J=7, 2 Hz), 5.71(2H, s), 3.83(3H, s)

MS m/e: 382(M$^+$), 381

EXAMPLE 56

5-(3-Methoxyphenyl)-3-benzyl-3H-imidazo[4,5-c]-[1,8]naphthyridin-4(5H)-one (Compound 56)

Melting point (solvent for recrystallization): 281°–282° C. (chloroform-isopropyl ether)

Elemental analysis (%): $C_{23}H_{18}N_4O_2$ Calcd.: C 72.24, H 4.74, N 14.65 Found: C 71.90, H 4.61, N 14.48

IR(KBr) vmax(cm$^{-1}$): 1667, 1515

$^1$H-NMR ($d_6$-DMSO) δ (ppm): 8.59(1H, s), 8.52(1H, dd, J=8, 2 Hz), 8.38(1H, dd, J=4, 2 Hz), 7.25–7.46(7H, m), 7.04(H, dd, J=8, 2 Hz), 6.84–6.91(2H, m), 5.72 (2H, s), 3.77(3H, s)

MS m/e: 382(M$^+$), 381

EXAMPLE 57

5-(4-Methylphenyl)-3-benzyl-3H-imidazo[4,5-c]-[1,8]naphthyridin-4(5H)-one (Compound 57)

Melting point (solvent for recrystallization): 253° C. (chloroform-isopropyl ether)

Elemental analysis (%): $C_{23}H_{18}N_4O$ Calcd.: C 75.39, H 4.95, N 15.29 Found: C 75.40, H 4.84, N 15.33

IR(KBr) vmax(cm$^{-1}$): 1664, 1574

$^1$H-NMR ($d_6$-DMSO) δ (ppm): 8.59(1H, s), 8.52(1H, dd, J=8, 2 Hz), 8.35(1H, dd, J=4, 2 Hz), 7.25–7.38(8H, m), 7.15(2H, d, J=8 Hz), 5.72(2H, s), 2.41(3H, s)

MS m/e: 366(M$^+$), 365

EXAMPLE 58

5-(3-Methylphenyl)-3-benzyl-3H-imidazo[4,5-c]-[1,8]naphthyridin-4(5H)-one (Compound 58)

Melting point (solvent for recrystallization): 190°–192° C. (chloroform-isopropyl ether)

Elemental analysis (%): $C_{23}H_{18}N_4O$ Calcd.: C 75.39, H 4.95, N 15.29 Found: C 75.38, H 5.06, N 15.17

IR(KBr) vmax(cm$^{-1}$): 1667, 936

$^1$H-NMR($d_6$-DMSO) δ (ppm): 8.60(1H, s), 8.52(1H, dd, J=8, 2 Hz), 8.37(1H, dd, J=4, 2 Hz), 7.24–7.44(7H, m), 7.04–7.09(2H, m), 5.71(2H, s), 2.36(3H, s)

MS m/e: 366(M$^+$), 365

EXAMPLE 59

5-(3-Chlorophenyl)-3-benzyl-3H-imidazo[4,5-c][1,8]naphthyridin-4(5H)-one (Compound 59)

Melting point (solvent for recrystallization): 228° C. (chloroform-isopropyl ether)

Elemental analysis (%): $C_{22}H_{15}N_4OCl$ Calcd.: C 68.31, H 3.91, N 14.48 Found: C 68.19, H 3.69, N 14.46

IR(KBr) vmax(cm$^{-1}$): 1668

$^1$H-NMR($d_6$-DMSO) δ (ppm): 8.61(1H, s), 8.53(1H, dd, J=8, 2 Hz), 8.38(1H, dd, J=4, 2 Hz), 7.48–7.57(3H, m), 7.25–7.40(7H, m), 5.72(2H, s)

MS m/e: 388, 387, 386(M$^+$), 385

EXAMPLE 60

2-Methyl-5-phenyl-3-benzyl-3H-imidazo[4,5-c] [1,8]-naphthyridin-4(5H)-one (Compound 60)

Melting point (solvent for recrystallization): 267°–269° C. (ethanol-water)

Elemental analysis (%): $C_{23}H_{18}N_4O$ Calcd.: C 75.39, H 4.95, N 15.29 Found: C 75.28 H 4.91, N 14.84

IR (KBr) vmax(cm$^{-1}$): 3648, 3362, 1615, 1594

$^1$H-NMR (d$_6$-DMSO) δ (ppm): 8.51 (1H, dd, J=8, 2Hz), 8.39 (1H, dd, J=4, 2 Hz), 7.19–7.56 (11H, m), 5.79 (2H, s), 2.52 (3H, s)

MS m/e: 368, 367, 366, 365(M$^+$)

EXAMPLE 61

2,5-Diphenyl-3-benzyl-3H-imidazo[4,5-c] [1,8] naphthyridin-4(5H)-one (Compound 61)

Melting point (solvent for recrystallization): 283°–287° C. (DMF-water)

Elemental analysis (%): $C_{28}H_{20}N_4O$ Calcd: C 78.49, H 4.70, N 13.08 Found: C 78.68, H 4.71, N 12.72

IR(KBr) vmax(cm$^{-1}$): 1664

$^1$H-NMR(d$_6$-DMSO) δ (ppm): 8.62 (1H, dd, J=8, 2Hz), 8.41 (1H, dd, J=4, 2Hz), 7.71 (2H, dd, J=7.18–7.61 (12H, m), 6.97 (2H, dd, J=7, 2Hz), 5.88 (2H, s)

MS m/e: 429, 428 (M$^+$), 427, 91

TABLE 10

| Compound | Starting Compound | Yield (%) |
|---|---|---|
| 55 | Compound 22 | 75 |
| 56 | Compound 23 | 84 |
| 57 | Compound 24 | 67 |
| 58 | Compound 25 | 40 |
| 59 | Compound 26 | 65 |
| 60 | Compound 18 | 70 |
| 61 | Compound 19 | 93 |

In Examples 62–65, the same procedure as in Example 12 was repeated except that the compounds shown in Table 11 were used respectively instead of Compound 3.

EXAMPLE 62

3-Isobutyl-5-(4-methoxyphenyl)-3H-imidazo[4,5-c] [1,8]naphthyridin-4(5H)-one (Compound 62)

Melting point (solvent for recrystallization): 232°–235° C. (chloroform-isopropyl ether)

Elemental analysis (%): $C_{20}H_{20}N_4O_2$ Calcd.: C 68.95, H 5.79, N 16.08 Found: C 68.67, H 5.86, N 15.86

IR(KBr) vmax(cm$^{-1}$): 1676, 1575

$^1$H-NMR(d$_6$-DMSO) δ (ppm): 8.51 (1H, dd, J=8, 2 Hz), 8.39 (1H, s), 8.36 (1H, dd, J= 4, 2 Hz), 7.35 (1H, dd, J= 8, 4 Hz), 7.20(2H, d, J=9 Hz), 7.06(2H, d, J=9 Hz), 4.26 (2H, d, J=7 Hz), 3.85 (3H, s), 2.09–2.24(1H, m), 0.87 (6H, d, J=7 Hz)

MS m/e: 348(M$^+$), 347, 292, 291

EXAMPLE 63

3-Isobutyl-5-(3-methoxyphenyl)-3H-imidazo[4,5-c] [1,8] naphthyridin-4 (5H)-one (Compound 63)

Melting point (solvent for recrystallization): 233°–234° C. (chloroform-isopropyl ether)

Elemental analysis (%): $C_{20}H_{20}N_4O_2$ Calcd.: C 68.94, H 5.78, N 16.08 Found: C 68.92, H 5.84, N 16.07

IR(KBr) vmax(cm$^{-1}$): 1668, 1511

$^1$H-NMR(d6-DMSO) δ (ppm): 8.52(1H, dd, J=8, 2 Hz), 8.41 (1H, s), 8.38(1H, dd, J=4, 2 Hz), 7.34– 7.47(2H, m), 7.04(1H, dd, J=8, 2 Hz), 6.85–6.92(2H, m), 4.26 (2H, d, J=7 Hz), 3.78(3H, s), 2.08–2.25(1H, m), 0.87 (6H, d, J=7 Hz)

MS m/e: 348(M$^+$), 347, 292, 291

EXAMPLE 64

3-Isobutyl-5-(4-methylphenyl)-3H-imidazo[4,5-c] [1,8] naphthyridin-4(5H)-one (Compound 64)

Melting point (solvent for recrystallization): 193°–195° C. (chloroform-isopropyl ether)

Elemental analysis (%): $C_{20}H_{20}N_4O \cdot 0.2H_2$ Calcd.: C 71.49, H 6.12, N 16.67 Found: C 71.39, H 6.01, N 16.42

IR (KBr) vmax (cm$^{-1}$): 1664, 1602, 1574

$^1$H-NMR(d$_6$-DMSO) δ (ppm): 8.52 (1H, dd, J=8, 2Hz), 8.40(1H, s), 8.36(1H, dd, J=4, 2 Hz), 7.31–7.37 (3H, m), 7.16 (2H, d, J=8Hz), 4.26 (2H, d, J=7 Hz), 2.42(3H, s), 2.08–2.24(1H, m), 0.86 (6H, d, J=7 Hz)

MS m/e: 332 (M$^+$), 331, 276, 275

EXAMPLE 65

3-Isobutyl-5-(3-methylphenyl)-3H-imidazo[4,5-c]-[1,8] naphthyridin-4 (5H)-one (Compound 65)

Melting point (solvent for recrystallization): 177°–178° C. (chloroform-isopropyl ether)

Elemental analysis (%): $C_{20}H_{20}N_4O \cdot 0.3H_2O$ Calcd.: C 71.11, H 6.15, N 16.59 Found: C 71.24, H 6.12, N 16.53

IR (KBr) vmax (cm$^{-1}$): 1662

$^1$H-NMR(d$_6$-DMSO) δ (ppm): 8.52 (1H, dd, J=8, 2 Hz), 8.40 (1H, s), 8.37(1H, dd, J=4, 2 Hz), 7.32–7.44 (2H, m), 7.27 (1H, d, J=7 Hz), 7.05–7.10 (2H, m), 4.26 (2H, d, J=7 Hz), 2.38(3H, s), 2.08–2.24 (1H, m), 0.87 (6H, d, J=7 Hz)

MS m/e: 332(M$^+$), 331, 276, 275

TABLE 11

| Compound | Starting Compound | Yield (%) |
|---|---|---|
| 62 | Compound 22 | 20 |
| 63 | Compound 23 | 6 |
| 64 | Compound 24 | 49 |
| 65 | Compound 25 | 4 |

EXAMPLE 66

3-(3-Morpholino)propyl-5-phenyl-3 H-imidazo[4,5-c] [1,8] naphthyridin-4 (5H)-one hydrochloride (Compound 66)

Morpholine (30 ml) was added to 2.0 g (4.7 mmol) of Compound 69 obtained in Example 69, and the mixture was stirred at room temperature for one hour. After addition of water, extraction was carried out with chloroform. The organic layer was removed by extraction with 2N hydrochloric acid. The water layer was adjusted to pH 11 with 8N sodium hydroxide, followed by extraction with chloroform. The organic layer was washed with a saturated aqueous solution of sodium chloride and dried over anhydrous sodium sulfate. After filtration, the solvent was evaporated under reduced pressure. To the obtained crude product was added ethyl acetate saturated with hydrogen chloride, and the formed crystals were taken by filtration and dried to give 1.0 g (yield 55%) of Compound 66.

Melting point: 294°–297° C.

Elemental analysis (%): $C_{22}H_{23}N_5O_2 \cdot 9 \; 2.0HCl \cdot 1.4H_2O$ Calcd.: C 54.19, H 5.79, N 14.36 Found: C 54.12, H 5.79, N 14.43

IR(KBr) vmax(cm$^{-1}$): 3676, 2346, 1695

$^1$H-NMR(d$_6$-DMSO) δ (ppm): 11.51(1H, br.s), 8.87(1H, s), 8.67 (1H, dd, J=8, 2 Hz), 8.40 (1H, dd, J=4, 2 Hz), 7.28–7.63(6H, m), 4.45 –4.80 (2H, m), 3.77–4.02 (4H, m), 3.32–3.49(2H, m), 2.92–3.22 (4H, m), 2.30–2.48 (2H, m)

MS m/e: 390, 389(M$^+$), 388, 276, 275, 100

EXAMPLE 67

3-(3-Diethylamino)propyl-5-phenyl-3H-imidazo-[4,5-c][1,8]naphthyridin-4(5H)-one hydrochloride (Compound 67)

Compound 67 was obtained according to the same procedure as in Example 66 except that diethylamine was used instead of morpholine (yield 69%).

Melting point: 152°–153° C.

Elemental analysis (%): $C_{22}H_{25}N_5O \cdot 0.2 \; HCl \cdot 1.3 \; H_2O$ Calcd.: C 56.01, H 6.32, N 14.84 Found: C 55.95, H 6.19, N 14.70

IR(KBr) vmax(cm$^{-1}$): 3734, 3688, 3676, 3648, 771

$^1$H-NMR(d$_6$-DMSO) δ (ppm): 10.57(2H, br.s), 8.68(1H, s), 8.60 (1H, dd, J=8, 2 Hz), 8.39 (1H, dd, J=4, 2 Hz), 7.22–7.60 (6H, m), 4.60 (2H, t, J=7 Hz), 2.91–3.14 (6H, m), 2.20–2.35 (2H, m), 1.18(6H, t)

MS m/e: 376, 375(M$^+$), 347, 346, 314, 303, 86

EXAMPLE 68

3-(3-Chloropropyl)-5-phenyl-3H-imidazo[4,5-c][1,8] naphthyridin-4(5H)-one (Compound 68)

Compound 68 was obtained according to the same procedure as in Example 4 except that 1-bromo-3-chloropropane was used instead of methyl iodide (yield 92%).

Melting point (solvent for recrystallization): 186°–190° C. (ethyl acetate-n-hexane)

Elemental analysis (%): $C_{18}H_{15}N_4OCl \cdot 0.2 \; H_2O$ Calcd.: C 63.14, H 4.53, N 16.36 Found: C 63.09, H 4.30, N 16.34

IR(KBr) vmax(cm$^{-1}$): 2958, 1650, 1575

$^1$H-NMR(CDCl$_3$) δ (ppm): 8.62 (1H, dd, J=8, 2 Hz), 8.41 (1H, dd, J=4, 2 Hz), 8.01(1H, s), 7.11–7.62(6H, m), 4.67(2H, t, J=7 Hz), 3.53(2H, t, J=7 Hz), 2.30–2.55 (2H, m)

MS m/e: 340, 339, 338 (M$^+$), 337

EXAMPLE 69

3-(3-Iodopropyl)-5-phenyl-3H-imidazo[4,5-c][1,8]naphthyridin-4(5H)-one (Compound 69)

To 200 ml of acetonitrile were added 18 g (0.052 mol) of Compound 68 obtained in Example 68 and 12 g (0.078 mol) of sodium iodide, and the mixture was refluxed for 24 hours. In the course of refluxing, 7.8 g (0.052 mol) of sodium iodide was added to the mixture. After cooling, the solvent was evaporated under reduced pressure and water was added to the residue. Then, extraction was carried out with chloroform, and the organic layer was washed with a saturated aqueous solution of sodium chloride and dried over anhydrous sodium sulfate. After filtration, the solvent was evaporated under reduced pressure to obtain a crude product. Recrystallization from ethyl acetate-nhexane gave 16 g (yield 73%) of Compound 69.

$^1$H-NMR (CDCl$_3$) δ (ppm): 8.59(1H, dd, J= 8, 2 Hz), 8.42 (1H, dd, J=4, 2 Hz), 8.03(1H, s), 7.28–7.72 (6H, m), 4.60 (2H, t, J=7 Hz), 3.12(2H, t, J=7 Hz), 2.30–2.61 (2H, m)

EXAMPLE 70 Tablets

Tablets each having the following composition, are prepared in a conventional manner.

| | |
|---|---|
| Compound 1 | 100 mg |
| Lactose | 60 mg |
| Potato starch | 30 mg |
| Polyvinyl alcohol | 2 mg |
| Magnesium stearate | 1 mg |
| Tar pigment | trace |

EXAMPLE 71 Powder

Powder having the following composition is prepared in a conventional manner.

| | |
|---|---|
| Compound 2 | 100 mg |
| Lactose | 300 mg |

EXAMPLE 72 Syrup

Syrup having the following composition is prepared in a conventional manner.

| | |
|---|---|
| Compound 1 | 100 mg |
| Refined sugar | 30 g |
| Ethyl p-hydroxybenzoate | 40 mg |
| Propyl p-hydroxybenzoate | 10 mg |
| Strawberry flavor | 0.1 cc |

Water is added to the composition to make the whole volume 100 cc.

EXAMPLE 73 Syrup

Syrup having the following composition is prepared in a conventional manner.

| | |
|---|---|
| Compound 2 | 100 mg |
| Refined sugar | 30 g |
| Ethyl p-hydroxybenzoate | 40 mg |
| Propyl p-hydroxybenzoate | 10 mg |
| Strawberry flavor | 0.1 cc |

Water is added to the composition to make the whole volume 100 cc.

The compounds obtained in Reference Examples are shown in Table 12.
TABLE 12-1
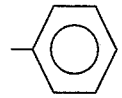
| Reference Example No. | Compound No. | $A_1$ | $A_2$ |
|---|---|---|---|
| 1 | a | —Cl | 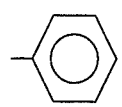 |
| 2 | b | —NHCH$_3$ | " |
| 3 | c | —NH$_2$ | " |
| 4 | d | —Cl | —(CH$_2$)$_3$CH$_3$ |
| 5 | e | —NHCH$_3$ | " |
| 6 | h | —NHC$_2$H$_5$ | 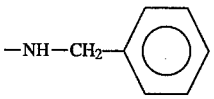 |
| 7 | i | —NH(CH$_2$)$_2$CH$_3$ | " |
| 8 | j | —NH—CH$_2$—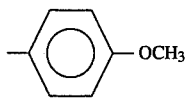 | " |
| 9 | k | —NH$_2$ | —(CH$_2$)$_3$CH$_3$ |
| 15 | m-1 | —OH | 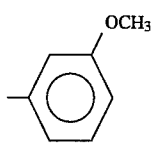  OCH$_3$ |
| 16 | m-2 | —OH | 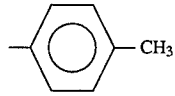 OCH$_3$ |
| 17 | m-3 | " | 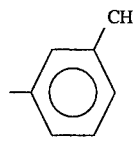—CH$_3$ |
| 18 | m-4 | " | 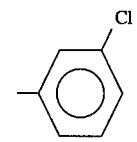 CH$_3$ |
| 19 | m-5 | " | 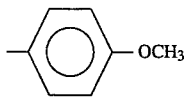 Cl |
| 20 | n-1 | —NH$_2$ | 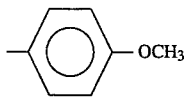 OCH$_3$ |

TABLE 12-1-continued

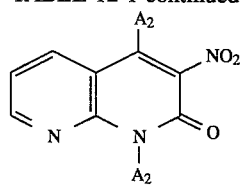

| Reference Example No. | Compound No. | $A_1$ | $A_2$ |
|---|---|---|---|
| 21 | n-2 | " | 3-OCH$_3$-phenyl |
| 22 | n-3 | " | 4-CH$_3$-phenyl |
| 23 | n-4 | " | 3-CH$_3$-phenyl |
| 24 | n-5 | " | 3-Cl-phenyl |

TABLE 12-2

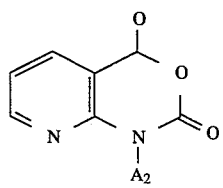

| Reference Example No. | Compound No. | $A_2$ |
|---|---|---|
| 10 | l-1 | 4-OCH$_3$-phenyl |
| 11 | l-2 | 3-OCH$_3$-phenyl |
| 12 | l-3 | 4-CH$_3$-phenyl |

TABLE 12-2-continued

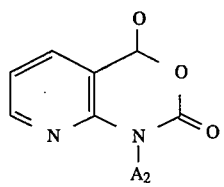

| Reference Example No. | Compound No. | $A_2$ |
|---|---|---|
| 13 | l-4 | 3-CH$_3$-phenyl |
| 14 | l-5 | 3-Cl-phenyl |

REFERENCE EXAMPLE 1

4-Chloro-3-nitro-1-phenyl-1,8-naphthyridin-2(H)-one (Compound a)

(A) 1-Phenyl-2H-pyrido[2,3-d][1,3]oxazine-2,4(1H)-dione (Compound p)

In a mixture of 70 ml of 1,2-dichloroethane and 7 ml of dioxane was dissolved 7.0 g (0.031 mol) of methyl 2-anilinonicotinate [J. Org. Chem., 39, 1803 (1974)]. After 11 ml (0.092 mol) of trichloromethyl chloroformate was added dropwise to the solution at 60° C. with stirring, the mixture was refluxed for 3 hours. The mixture was slightly cooled and 0.25 g of activated carbon was added thereto, followed by refluxing for further 30 minutes in a nitrogen flow. The mixture was cooled to room temperature, filtered and concentrated to form crystals. Recrystallization from methylene chloride-isopropyl ether gave 6.5 g (yield 87%) of 1-phenyl-2H-pyrido [2,3-d] [1,3]oxazine-2,4( 1H)-dione (Compound p) as colorless crystals.

Melting point: 196°–198° C.

Elemental analysis (%): $C_{13}H_8N_2O_3$ Calcd.: C 65.00, H 3.36, N 11.66 Found: C 65.11, H 3.22, N 11.48

IR(KBr) vmax(cm$^{-1}$): 1791, 1727, 1584

$^1$H-NMR(CDCl$_3$) δ (ppm): 8.58(1H, dd, J=5, 2 Hz), 8.48 (1H, dd, J=8, 2Hz), 7.51–7.63(3H, m), 7.33–7.38 (2H, m), 7.29(1H, dd, J=8, 5 Hz)

MS m/e: 240(M$^+$), 196, 168

(B) 4-Hydroxy-3-nitro-1-phenyl-1,8 -naphthyridin-2(1H)-one (Compound f)

In 25 ml of N,N-dimethylacetamide was dissolved 1.9 ml (0.020 mol) of ethyl nitroacetate, and 0.80 g (0.020 moi) of 60% sodium hydride was added to the solution under ice cooling. After evolution of hydrogen ceased, 4.0 g (0.017 mol) of Compound p obtained was added and the mixture was slowly heated, followed by stirring at 100° C. for 30 minutes. The solvent was distilled off under reduced pressure and 200 ml of water was added to the residue. After washing with ethyl acetate, the aqueous layer was made acidic with conc. hydrochloric acid. The precipitated crystals were taken by filtration. Recrystallization from isopropyl alcohol-ethanol gave 3.6 g (yield 77%) of 4-hydroxy-3-nitro-1-phenyl-1,8-naphthyridin- 2(1H)-one (Compound f) as light yellow needles.

Melting point: 296°–298° C.

Elemental analysis (%): $C_{14}H_9N_3O_4$ Calcd.: C 59.37, H 3.20, N 14.84 Found: C 59.57, H 2.99, N 14.68

IR(KBr) vmax(cm$^{-1}$): 1682, 1587, 1410

$^1$H-NMR(d$_6$-DMSO) δ (ppm): 8.50(1H, dd, J=8, 2 Hz), 8.48 (1H, dd, J=4, 2 Hz), 7.41–7.54(3H, m), 7.26–7.36 (3H, m)

MS m/e: 283(M$^+$), 282, 265, 77

(C) 4-Chloro-3-nitro-1-phenyl-1,8 -naphthyridin-2(1H)-one (Compound a)

Compound f obtained (10 g, 0.038 mol) was suspended in 50 ml (0.54 mol) of phosphorus oxychloride, and the suspension was heated at 100° C. for one hour. After the solvent was distilled off under reduced pressure, 4N sodium hydroxide solution was added under ice cooling for neutralization. The precipitated crystals were taken by filtration to give 5.2 g (yield 49%) of Compound a as white crystals.

Melting point (solvent for recrystallization): 228°–232° C. (ethyl acetate-n-hexane)

Elemental analysis (%): $C_{14}H_8ClN_3O_3$ Calcd.: C 55.74, H 2.21, N 13.63 Found: C 55.91, H 2.68, N 13.97

IR(KBr) vmax(cm$^{-1}$): 1667, 1587, 1547

$^1$H-NMR(CDCl$_3$) δ (ppm): 8.62 (1H, dd, J=4, 2 Hz), 8.54 (1H, dd, J=8, 2 Hz), 8.50–8.65(3H, m), 7.41(1H, dd, J=8, 4 Hz), 7.25–7.33 (2H, m)

MS m/e: 300, 302 (M$^+$)

REFERENCE EXAMPLE 2

4-Methylamino-3-nitro-1-phenyl-1,8 -naphthyridin-2(1H) -one (Compound b)

In 60 ml of tetrahydrofuran was dissolved 1.8 g (6.0 mmol) of Compound a obtained in Reference Example 1, and 4.6 ml (60 mmol) of 40% aqueous solution of methylamine was added to the solution, followed by stirring at room temperature for 30 minutes. The solvent was distilled off under reduced pressure and 100 ml of water was added to the residue. The precipitated crystals were taken by filtration and dried to give 1.6 g (yield 97%) of Compound b as light yellow crystals.

Melting point (solvent for recrystallization): >300° C. (DMF-water)

Elemental analysis (%): $C_{15}H_{12}N_4O_3$ Calcd.: C 60.93, H 3.94, N 19.07 Found: C 60.81, H 4.08, N 18.71

IR(KBr) vmax(cm$^{-1}$): 1620, 1588

$^1$H-NMR(d$_6$-DMSO) δ (ppm): 8.64(1H, dd, J=8, 2 Hz), 8.45 (1H, dd, J=4, 2 Hz), 8.05–8.16 (1H, m), 7.42–7.55 (3H, m), 7.37(1H, dd, J=8, 4 Hz), 7.22–7.29(2H, m), 2.88 (3H, d, J=5Hz)

MS m/e: 296(M$^+$), 261

REFERENCE EXAMPLE 3

4-Amino-3-nitro-1-phenyl-1,8 -naphthyridin-2(1H)-one (Compound c)

Compound c was obtained as light yellow crystals according to the same procedure as in Reference Example 2 except that aqueous ammonia was used instead of methylamine (yield 86%).

Melting point: >300° C.

REFERENCE EXAMPLE 4

1-(n-Butyl)-4-chloro-3-nitro-1,8 -naphthyridin-2(1H)-one (Compound d)

Phosphorus oxychloride (20 ml, 0.21 mol) was added to 2.0 g (7.6 mmol) of 1-n-butyl-4 -hydroxy-3-nitro- 1,8-naphthyridin-2(1H)-one [J. Heterocyclic Chem., 22, 193 (1985)], and the mixture was heated to reflux for 30 minutes. After cooling to room temperature, the solvent was distilled off under reduced pressure and ice water was added to the resulting residue. The mixture was neutralized with 4N aqueous solution of sodium hydroxide, followed by extraction with chloroform. The organic layer was dried over anhydrous sodium sulfate, and then filtered. The solvent was distilled off under reduced pressure. The obtained residue was purified by silica gel column chromatography (developing solvent: chloroform/methanol= 20/1) to give 1.2 g (yield 56%) of Compound d as colorless crystals.

Elemental analysis (%): $C_{12}H_{12}ClN_3O_3$ Calcd.: C 51.30, H 4.02, N 14.93 Found: C 51.16, H 4.29, N 14.92

$^1$H-NMR(CDCl$_3$) δ (ppm): 8.78 (1H, dd, J=4, 2 Hz), 8.38 (1H, dd, J=8, 2 Hz), 7.39(1H, dd, J=8, 4 Hz), 4.56 (2H, t, J=7 Hz), 1.25–1.76(4H, m), 0.97(2H, t, J=7 Hz)

MS m/e: 266, 264(M$^+$—OH), 208, 206

REFERENCE EXAMPLE 5

1-(n-Butyl)-4-methylamino-3-nitro-1,8-naphthyridin-2(1H)-one (Compound e)

Compound e was obtained as light yellow crystals in an amount of 2.7 g (yield 90%) according to the same procedure as in Reference Example 2 except that 3 g (11 mmol) of Compound d obtained in Reference Example 4 was used instead of Compound a.

Elemental analysis (%): $C_{13}H_{16}N_4O_3$ Calcd.: C 56.57, H 5.87, N 20.41 Found: C 56.51, H 5.84, N 20.28

$^1$H-NMR($d_6$-DMSO) δ (ppm): 8.71(1H, dd, J=4, 2 Hz), 8.58 (1H, dd, J=8, 2 Hz), 7.75–8.02 (1H, m), 7.38 (1H, dd, J=8, 4 Hz), 4.31(2H, t, J=7 Hz), 1.12–1.79(4H, m), 0.91 (3H, t, J=7 Hz)

MS (m/e): 259 (M$^+$—OH), 241, 187

REFERENCE EXAMPLE 6

4-Ethylamino-3-nitro-1-phenyl-1,8-naphthyridin-2(1H)-one (Compound h)

Compound h was obtained according to the same procedure as in Reference Example 2 except that ethylamine was used instead of methylamine.

Melting point (solvent for recrystallization): 189°–193° C. (DMF-water)

Elemental analysis (%): $C_{16}H_{14}N_4O_3$ Calcd.: C 61.79, H 4.53, N 17.78 Found: C 61.93, H 4.55, N 18.06

IR(KBr) vmax(cm$^{-1}$): 1617

$^1$H-NMR ($d_6$-DMSO) δ (ppm): 8.72 (1H, dd, J=8, 2 Hz), 8.42 (1H, dd, J=4, 2 Hz), 7.06–7.71 (6H, m), 3.11–3.29 (2H, m), 1.26(3H, t, J=7 Hz)

MS (m/e): 310 (M$^+$), 297, 275

REFERENCE EXAMPLE 7

4-Isopropylamino-3-nitro-1-phenyl-1,8-naphthyridin-2(1H)-one (Compound i)

Compound i was obtained according to the same procedure as in Reference Example 2 except that isopropylamine was used instead of methylamine.

Melting point (solvent for recrystallization): 257°–261° C. (ethanol-water)

Elemental analysis (%): $C_{17}H_{16}N_4O_3$ Calcd.: C 63.19, H 4.86, N 17.04 Found: C 62.97, H 4.97, N 17.27

IR(KBr) vmax(cm$^-$): 1659, 1607

$^1$H-NMR(d6-DMSO) δ (ppm): 8.51 (1H, dd, J=4, 2 Hz), 8.20 (1H, dd, J=8, 2 Hz), 7.42–7.58(3H, m), 7.23–7.29 (2H, m), 7.21(1H, dd, J=8, 4 Hz), 6.93–7.05(1H, m), 4.02–4.20(1H, m), 1.40(6H, d, J=6 Hz)

MS(m/e): 324(M$^+$), 306, 289, 222

REFERENCE EXAMPLE 8

4-Benzylamino-3-nitro-1-phenyl-1,8-naphthyridin-2(1H)-one (Compound j)

Compound j was obtained according to the same procedure as in Reference Example 2 except that benzylamine was used instead of methylamine.

Melting point (solvent for recrystallization): 192°–194° C. (methanol-water)

Elemental analysis (%): $C_{21}H_{16}N_4O_3$ Calcd.: C 68.13, H 4.24, N 14.91 Found: C 67.73, H 4.33, N 15.04

IR(KBr) vmax(cm$^{-1}$): 1616, 1519

$^1$H-NMR($d_6$-DMSO) δ (ppm): 8.80(1H, dd, J=8, 2 Hz), 8.49 (1H, dd, J=4, 2 Hz), 8.25–8.41(1H, br. s), 7.18–7.56 (11H, m), 4.44 (2H, s)

MS (m/e): 372 (M$^+$), 326, 91

REFERENCE EXAMPLE 9

4-Amino-1-n-butyl-3-nitro-1,8-naphthyridin-2(1H)-one (Compound k)

Compound k was obtained according to the same procedure as in Reference Example 5 except that aqueous ammonia was used instead of methylamine.

Elemental analysis (%) : $C_{12}H_{14}N_4O_3$ Calcd.: C 55.07, H 5.40, N 4.36 Found: C 54.96, H 5.38, N 21.36

$^1$H-NMR ($d_6$-DMSO) δ (ppm): 8.55–8.78 (2H, m), 8.23 (1H, br.s), 7.31(1H, dd, J=8, 4 Hz), 4.27 (2H, t, J=7 Hz), 1.15–1.70 (4H, m), 0.91 (3H, t, J=7 Hz)

MS (m/e): 245 (M$^+$ —OH)

In Reference Examples 10–14, the same procedure as in Reference Example 1-A was repeated except that the compounds shown in Table 13 were used respectively instead of methyl 2-anilinonicotinate.

REFERENCE EXAMPLE 10

1-(4-Methoxy)phenyl-2H-pyrido[2,3-d] [1,3]oxazine-2,4(1H)-dione (Compound l-1)

Melting point: 230°–233° C.

REFERENCE EXAMPLE 11

1-(3-Methoxy)phenyl-2H-pyrido[2,3-d][1,3]oxazine-2,4(1H)-dione (Compound l-2)

Melting point: 233°–245° C.

REFERENCE EXAMPLE 12

1-(4-Methyl)phenyl-2H-pyrido[2,3-d] [1,3]oxazine-2,4(1H)-dione (Compound l-3)

Melting point: 240°–245° C.

REFERENCE EXAMPLE 13

1-(3-Methyl)phenyl-2H-pyrido[2,3-d][1,3]oxazine-2,4(1H)-dione (Compound l-4)

Melting point: 151°–154° C.

REFERENCE EXAMPLE 14

1-(3-Chloro)phenyl-2H-pyrido[2,3-d] [1,3]oxazine-2,4(1H)-dione (Compound l-5)

Melting point: 230°–233° C.

TABLE 13

| Reference Example No. | Compound | Yield (%) |
| --- | --- | --- |
| 10 | Methyl 2-(4-Methoxy)anilinonicotinate | 92 |
| 11 | Methyl 2-(3-Methoxy)anilinonicotinate | 72 |
| 12 | Methyl 2-(4-Methyl)anilinonicotinate | 93 |

TABLE 13-continued

| Reference Example No. | Compound | Yield (%) |
| --- | --- | --- |
| 13 | Methyl 2-(3-Methyl)anilinonicotinate | 79 |
| 14 | Methyl 2-(3-Chloro)anilinonicotinate | 72 |

In Reference Examples 15–19, the same procedure as in Reference Example 1-B as repeated except that the compounds shown in Table 14 were used respectively instead of Compound p.

REFERENCE EXAMPLE 15

4-Hydroxy-1-(4-methoxy)phenyl-3-nitro-1,8-naphthyridin-2(1H)-one (Compound m-1)

Melting point: 220°–222° C.

REFERENCE EXAMPLE 16

4-Hydroxy-1-(3-methoxy)phenyl-3-nitro-1,8-naphthyridin2( 1H)-one (Compound m-2)

Melting point: 216°–217° C.

REFERENCE EXAMPLE 17

4-Hydroxy-1-(4-methyl)phenyl-3-nitro-1,8-naphthyridin-2(1H )-one (Compound m-3)

Melting point: 225°–226° C.

REFERENCE EXAMPLE 18

4-Hydroxy-11-(3-methyl)phenyl-3-nitro-1,8-naphthyridin-2( 1H)-one (Compound m-4)

Melting point: 206° C.

REFERENCE EXAMPLE 19

4-Hydroxy-1-(3-chloro)pheny-l3-nitro-1,8-naphthyridin-2(1H )-one (Compound m-5 )

Melting point: 189°–191° C.

TABLE 14

| Reference Example No. | Starting Compound (Number of Reference Example wherein the above compound is obtained) | Yield (%) |
| --- | --- | --- |
| 15 | 1 - 1 (10) | 50 |
| 16 | 1 - 2 (11) | 66 |
| 17 | 1 - 3 (12) | 78 |
| 18 | 1 - 4 (13) | 69 |
| 19 | 1 - 5 (14) | 74 |

In Reference Examples 20–24, the same procedure as in Reference Example 1-C was repeated except that the compounds shown in Table 15 were used respectively instead of Compound f.

REFERENCE EXAMPLE 20

4-Amino-1-(4-methoxy)phenyl-3-nitro-1,8-naphthyridin-2(1H)-one (Compound n-1)

Melting point: >300° C.

REFERENCE EXAMPLE 21

4-Amino-1-(3-methoxy)phenyl-3-nitro-1,8-naphthyridin-2(1H)-one (Compound n-2)

Melting point: >300° C.

REFERENCE EXAMPLE 22

4-Amino-1-(4-methyl)phenyl-3-nitro-1,8-naphthyridin-2(1H)-one (Compound n-3)

Melting point: >300° C.

REFERENCE EXAMPLE 23

4-Amino-1-(3-methyl)phenyl-3-nitro- 1,8-naphthyridin-2(1H)-one (Compound n-4 )

Melting point: >300° C.

REFERENCE EXAMPLE 24

4-Amino-1-(3-chloro)phenyl-3-nitro-1,8-naphthyridin-2(1H)- one (Compound n-5)

Melting point: >300° C.

TABLE 15

| Reference Example No. | Starting Compound (Number of Reference Example wherein the above compound is obtained) | Yield (%) |
| --- | --- | --- |
| 20 | m - 1 (15) | 78 |
| 21 | m - 2 (16) | 85 |
| 22 | m - 3 (17) | 84 |
| 23 | m - 4 (18) | 85 |
| 24 | m - 5 (19) | 70 |

What is claimed is:

1. An imidazonaphthyridine derivative represented by formula (I):

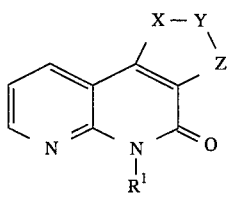

wherein:

R$^1$ represents lower alkyl or substituted or unsubstituted aryl; and

X—Y—Z represents

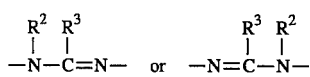

wherein $R^2$ represents —C($R^5$)H—(CH$_2$)$_n$—$R^4$ (wherein $R^4$ represents substituted or unsubstituted aryl group having 6–10 carbon atoms, hydroxy-substituted lower alkyl, lower alkanoyloxy, lower alkanoyl, carboxy, lower alkoxycarbonyl, cycloalkyl, hydroxy, lower alkoxy, halogen or N$R^6R^7$ wherein $R^6$ and $R^7$ independently represents hydrogen or lower alkyl; $R^5$ represents hydrogen, lower alkyl, or phenyl; and n represents an integer of 0 to 3); and $R^3$ represents hydrogen, mercapto, hydroxy, lower alkyl, or aryl or a pharmaceutically acceptable salt thereof.

2. A compound according to claim 1, wherein X—Y—Z is

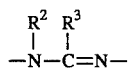

wherein $R^3$ is hydrogen.

3. A compound according to claim 1, wherein X—Y—Z is

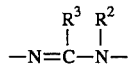

wherein $R^2$ is —C($R^5$)H—(CH$_2$)$_n$—$R^4$ (wherein $R^4$ represents substituted or unsubstituted aryl, lower alkanoyloxy, lower alkoxycarbonyl, lower alkanoyl or lower alkoxy; $R^5$ represents hydrogen; and n is 0 or 1) and $R^3$ represents hydrogen.

4. A compound according to claim 3, wherein $R^1$ is lower alkyl or phenyl; and $R^2$ is —CH$_2R^4$ (wherein $R^4$ is aryl, or lower alkanoyl).

5. A compound according to claim 1, which is selected from the group consisting of 5-(n-butyl)-1-methyl-1H-imidazo[4,5 -c] [1,8]naphthyridin- 4(5H)-one, 5-phenyl-3H-imidazo[4,5-c] [1,8] naphthyridin-4(5H)-one, 3-ethyl-5-phenyl-3H-imidazo[ 4,5-c] [ 1,8] naphthyridin-4(5H)-one, 5-phenyl-3-n-propyl-3H-imidazo[4,5-c] [ 1,8] naphthyridin- 4(5H)-one, 3-benzyl-5-phenyl-3H-imidazo[4,5-c] [1,8]naphthyridin-4(H)-one 3-acetyl-5-phenyl-3H-imidazo[ 4,5-c] [ 1,8] naphthyridin-4(5H)-one and 5-n-butyl-3-n-propyl-3H-imidazo[ 4,5-c] [ 1,8] naphthyridin- 4(5H )-one.

6. A compound according to claim 1, wherein said salt is an acid addition salt, a metal salt, an ammonium salt, an organic amine addition salt or an amino acid addition salt.

7. A pharmaceutical composition comprising a pharmaceutical carrier and, as an active ingredient, an effective amount of the compound as defined by claim 1.

* * * * *

UNITED STATES PATENT AND TRADEMARK OFFICE
CERTIFICATE OF CORRECTION

PATENT NO. : 5,468,756

DATED : November 21, 1995

INVENTOR(S): FUMIO SUZUKI ET AL.  Page 1 of 4

It is certified that error appears in the above-identified patent and that said Letters Patent is hereby corrected as shown below:

ON THE TITLE PAGE:

AT [57] ABSTRACT

Line 15, "represents" should read --represent--.

COLUMN 1

Line 3 should be deleted.
    Line 8, "doned." should read --doned.
        BACKGROUND OF THE INVENTION--.
    Line 50, "morpholino." should read --morpholino,--.
    Line 53, "represents" should read --represent--.

COLUMN 11

Table 1-2 Continued, Compound No. 27,
        "-CH$_2$)$_3$CH$_3$" should read -- -(CH$_2$)$_3$CH$_3$--.

COLUMN 20

Line 35, "IgC" should read --IgG--.

COLUMN 25

Line 18, "Recrystalllization" should read
        --Recrystallization--.
    Line 56, "3 0 ml" should read --30 ml--.

UNITED STATES PATENT AND TRADEMARK OFFICE
CERTIFICATE OF CORRECTION

PATENT NO. : 5,468,756

DATED : November 21, 1995

INVENTOR(S): FUMIO SUZUKI ET AL.

It is certified that error appears in the above-identified patent and that said Letters Patent is hereby corrected as shown below:

COLUMN 26

Line 4, "C 6 9.85," should read --C 69.85,--.
Line 23, "N 19 33" should read --N 19.33--.
Line 46, "H-NMR" should read --$^1$H-NMR--.

COLUMN 28

Line 10, "C 7" should read --C--.
Line 11, "1.15," should read 71.15,-- and
"C 7 1.28," should read --C 71.28,--.

COLUMN 35

Line 20, "104 -10 5°" should read --104°-105°--.

COLUMN 37

Line 42, "C 7 2.24," should read --C 72.24,--.
Line 43, "C 7 2.11," should read --C 72.11,--.

COLUMN 38

Line 23, "C 6 8.39," should read --C 68.39,--.

UNITED STATES PATENT AND TRADEMARK OFFICE
CERTIFICATE OF CORRECTION

PATENT NO. : 5,468,756

DATED : November 21, 1995

INVENTOR(S) : FUMIO SUZUKI ET AL.

Page 3 of 4

It is certified that error appears in the above-identified patent and that said Letters Patent is hereby corrected as shown below:

COLUMN 43

Line 31, "J=7.18-7.61" should read --J=7, 2Hz), 7.18-7.61--.

COLUMN 45

Line 35, "$\nu$max(cm$^{-1}$):" should read --$\nu$max(cm$^{-1}$):--.

COLUMN 46

Line 10, "acetate-nhexane" should read --acetate-n-hexane--.

COLUMN 51

Line 26, "moi)" should read --mol)--.

COLUMN 54

Line 39, "233°-245°C." should read --233°-235°C.--.

COLUMN 55

Line 38, "4-Hydroxy-11-" should read --4-Hydroxy-1- --.
Line 45, "pheny-13-" should read --phenyl-3- --.

UNITED STATES PATENT AND TRADEMARK OFFICE
CERTIFICATE OF CORRECTION

PATENT NO. : 5,468,756

DATED : November 21, 1995

INVENTOR(S) : FUMIO SUZUKI ET AL.

It is certified that error appears in the above-identified patent and that said Letters Patent is hereby corrected as shown below:

COLUMN 57

Line 12, "represents" should read --represent--.

COLUMN 58

Line 3, "or 1)" should read --or 1);--.

Signed and Sealed this

Ninth Day of July, 1996

Attest:

BRUCE LEHMAN

Attesting Officer

Commissioner of Patents and Trademarks